(12) United States Patent
Hayase et al.

(10) Patent No.: US 8,133,214 B2
(45) Date of Patent: Mar. 13, 2012

(54) MATERIAL REMOVAL CATHETER AND METHOD

(76) Inventors: Motoya Hayase, Boston, MA (US); J. Christopher Flaherty, Topsfield, MA (US)

(*) Notice: Subject to any disclaimer, the term of this patent is extended or adjusted under 35 U.S.C. 154(b) by 226 days.

(21) Appl. No.: 12/246,995

(22) Filed: Oct. 7, 2008

(65) Prior Publication Data

US 2009/0036871 A1 Feb. 5, 2009

Related U.S. Application Data

(63) Continuation of application No. 10/615,122, filed on Jul. 8, 2003, now Pat. No. 7,449,010.

(60) Provisional application No. 60/396,042, filed on Jul. 15, 2002.

(51) Int. Cl.
*A61M 1/00* (2006.01)
(52) U.S. Cl. .......................... 604/540; 604/19
(58) Field of Classification Search .............. 604/19, 604/27, 28, 48, 73, 76, 93.01, 95.01, 104–107, 604/128, 158, 264, 523, 540–544; 606/7, 606/13–17, 41, 46, 47, 167, 185; 607/101, 607/122
See application file for complete search history.

(56) References Cited

U.S. PATENT DOCUMENTS

| | | | |
|---|---|---|---|
| 3,081,770 A | | 3/1963 | Hunter |
| 5,007,434 A | * | 4/1991 | Doyle et al. ................. 600/585 |
| 5,232,440 A | * | 8/1993 | Wilk ............................. 604/543 |
| 5,242,460 A | | 9/1993 | Klein et al. |
| 5,269,757 A | * | 12/1993 | Fagan et al. ................ 604/95.01 |
| 5,419,764 A | | 5/1995 | Roll |
| 5,855,577 A | * | 1/1999 | Murphy-Chutorian et al. .. 606/7 |
| 6,017,323 A | | 1/2000 | Chee |
| 6,325,798 B1 | | 12/2001 | Edwards et al. |
| 6,527,737 B2 | | 3/2003 | Kaneshige |
| 6,942,641 B2 | * | 9/2005 | Seddon ........................ 604/107 |
| 2003/0060806 A1 | * | 3/2003 | Ikeguchi ..................... 604/540 |

* cited by examiner

*Primary Examiner* — Tatyana Zalukaeva
*Assistant Examiner* — Benedict L Hanrahan
(74) *Attorney, Agent, or Firm* — Onello & Mello, LLP

(57) ABSTRACT

A catheter device and methods useable to extract material from a body conduit, e.g., a blood vessel, are provided. The catheter comprises a flexible catheter advanceable into the body conduit, an opening in a wall of the catheter in fluid communication with a material collection chamber, and a controllably arcuate segment near the distal tip of the catheter and the opening. The catheter may include a sliding member, located within a lumen of the catheter, used to move the material entering the catheter through the arcuate segment opening, into the material collection chamber and away from said opening. The catheter may include a single mechanism utilized to both generate a vacuum to cause material to enter the catheter at the arcuate segment opening and also cause the sliding member to travel, inside the catheter, moving material away from the opening and into the material collection chamber.

8 Claims, 9 Drawing Sheets

MATERIAL REMOVAL CATHETER AND METHOD

CROSS REFERENCE TO RELATED APPLICATION

This application is a continuation application of U.S. patent application Ser. No. 10/615,122, filed Jul. 8, 2003, which relies for priority upon U.S. Provisional Patent Application Ser. No. 60/396,042, filed Jul. 15, 2002, now expired, entitled MATERIAL REMOVAL CATHETER AND METHOD.

FIELD OF THE INVENTION

The present invention relates generally to medical devices, systems and methods and more particularly to a material removal catheter and methods that are useable to remove thrombus and other undesired material from the vasculature or other internal conduit of a patient, the apparatus being particularly well suited for saphenous vein grafts, coronary arteries and the peripheral vasculature.

BACKGROUND OF THE INVENTION

Human blood vessels often become partly or fully occluded by various undesired materials including plaque, thrombi or other substances that restrict the flow of blood within the vessel. Depending on the location of the occlusion, serious injury or even death can occur. When diagnosed, it is often advantageous to remove the occlusive material in a safe and effective manner. Coronary heart disease is an extremely common form of this occlusive disease, and is the leading cause of death in the United States.

Arteriosclerosis is a chronic disease characterized by abnormal thickening and hardening of the arterial walls. As the coronary arteries are first narrowed by plaque, at locations known as stenoses, further constriction may be caused by the formation of blood clots, or thrombi, on the rough surface of the plaque. A severe complication of arteriosclerosis is a myocardial infarction, or MI. An MI is the death of a section of heart muscle when its blood supply is cut off, usually by a blood clot in a coronary artery narrowed by arteriosclerosis. An MI can occur spontaneously due to severely narrowed vasculature or due to an embolus, such as a thrombus released from an upstream stenosis. An embolus can even be caused in a medical procedure intended to reduce or remove a stenosis.

Various types of interventional techniques have been developed that can be utilized to reduce or remove a blockage in a blood vessel. One technique, known as balloon angioplasty, involves using a special catheter that includes a balloon near its distal tip, advancing the balloon into the constricted area, and inflating the balloon to expand the constriction. Other therapeutic options include atherectomy, deployment of stents, infusion of therapeutic medications and heart bypass surgery. All of these therapeutic options involve the risk of dislodging a portion of the occlusive material, causing embolus to move downstream thus causing further complications.

Heart bypass surgery is an extremely invasive and traumatic form of therapy to treat coronary occlusive disease. In one form of bypass, a portion of vein taken from the patient's leg, the saphenous vein, is connected between the aorta and a portion of the blocked artery distal to the blockage, supplying oxygenated blood to the portions of heart muscle supplied by the artery prior to its being occluded. These saphenous vein grafts often used in heart bypass procedures are also susceptible to occlusive disease, and over time may become restricted by plaque and thrombus. Atherosclerotic plaque in saphenous vein grafts tends to be softer and more friable than their arterial counterparts and thus more prone to embolizing during treatment.

Chemical thrombolytic drugs are available to treat saphenous vein grafts but require the patient to be non-ambulatory throughout their use and have numerous risks and complications. Balloon angioplasty of saphenous vein grafts is associated with a higher rate of embolus generation, potentially migrating downstream to block a portion of the coronary artery to which it is attached and causing a myocardial infarction. Directional Coronary Atherectomy, or DCA catheters include cutting blades that can damage the vessel wall and the systems have a propensity to become clogged and generate embolus similar to balloon angioplasty. Adjunctive devices are available to reduce the complications of embolization by trapping the released emboli downstream. These devices are expensive, and complicated to use. Vacuum extraction catheters have been developed to treat saphenous vein grafts, however they tend to be large and bulky and have had sub optimal results and numerous complications.

Clearly, therefore, there is a need for improved devices, systems and methods for removal of undesired material from an internal body conduit such as a saphenous vein graft or coronary artery that improve the efficiency of material removal and reduce the risks to the patient.

SUMMARY OF THE INVENTION

The present invention is directed to a device and method that simply and effectively removes undesired material from the wall of a conduit, such as a blood vessel. The device is a catheter with an elongate catheter shaft having a proximal end and a distal end. The distal end of the catheter shaft has a diameter less than the conduit containing the undesired material, said catheter shaft including a controllably arcuate portion or segment which can be directed toward and make contact with the undesired material prior to extraction. The controllably arcuate segment includes one or more openings into which the material is drawn by applying a negative pressure, or suction from the inside of the opening. The controllably arcuate segment can be transformed into both a relatively straight and a relatively bowed geometry with operator controls contained on the proximal end of the catheter device.

The catheter device of the present invention may be inserted into various body conduits including but not limited to blood vessels such as coronary vessels, peripheral vessels, coronary bypass grafts and arteriovenous fistulas. The device may be used for diagnostic applications, such as taking a material sample, or therapeutic applications such as reducing an occlusion within a saphenous vein graft. The device can be used in various hospital and outpatient settings, and can be guided using fluoroscopy and other imaging technologies. The device may include various markers or other visualization elements, such as radiopaque fillings or bands, ultrasound crystals or ultrasonic markers, or other markers or indicators to aid in positioning and use of the device. Such markers may include rotational orientation markers to indicate the position of one or more openings in the controllably arcuate segment. In addition or alternatively, the catheter device may include an arcuate condition indicator providing visual or other feedback to the operator as to the relatively straight or relatively bowed geometric conditions of the controllably arcuate segment. In a preferred embodiment, an audio signal is provided, such as when the controllably arcuate segment is in the relatively bowed geometry, to prevent the clinician from inadvertently advancing or otherwise moving the catheter shaft when the controllably arcuate segment should be in a relatively straight geometry. In another preferred embodiment, the catheter device includes a lumen, included along a minority or a majority of the length of the catheter shaft, through which a guidewire can be inserted for practice of over the wire interventional techniques.

The openings in the controllably arcuate segment of the device are in fluid communication with one or more ports or chambers in the proximal, external portion of the device via one or more lumens. Within or at the end of the lumens may exist one or more valves oriented to permit flow of material in one direction only. Located in a distal portion of the catheter, near to and in fluid communication with the openings is a material collection chamber. The material collection chamber is proximal or distal to the openings, and is in fluid communication with the proximal, aspirating portion of the device via a connecting lumen. In a preferred embodiment, the material collection chamber is the connecting lumen itself. Suction applied to the aspiration portion is communicated to the openings in the controllably arcuate segment via the material collection chamber.

In a preferred embodiment, the aspiration chamber may be connected to a waste exit, such as by a one-way valve such that when positive pressure is applied, material collected in the aspiration chamber from the openings in the controllably arcuate segment is evacuated from the aspiration chamber.

In a preferred embodiment, within a lumen of the catheter shaft is a sliding member that is connected to a mechanical linkage extending through the catheter shaft to the proximal portion of the device. The linkage is connected to sliding or other controls on the handle of the catheter device for advancement and retraction of the sliding member. In a preferred embodiment, the sliding member and mechanical linkage include a lumen permitting a guidewire to be placed through each. The linkage system may include one or more mechanical stops that limit the advancement or retraction. In the fully advanced position, the tip of the sliding member, which preferably is tapered, extends beyond the distal end of the catheter. The tip of the sliding member may extend beyond the end of the catheter in the fully retracted position as well. The sliding member can be used to change the geometry of the controllably arcuate segment. In a preferred embodiment, the controllably arcuate segment is normally bowed, and placing the sliding member within the lumen of the controllably arcuate segment changes the segment into a relatively straight geometry. To facilitate the change in shape of the controllably arcuate segment, the sliding member is constructed to be less flexible than the controllably arcuate segment. The sliding member, which may have a sharpened end that is oriented toward the opening, is advanced or retracted to move toward the opening thereby cutting and or pushing material away from the opening and into the material collection chamber. The one or more openings can have different cross sectional profiles, such as round or oval perimeters, or various angles of tapers, and may change geometry based on the geometry of the controllably arcuate segment and or the position of the sliding member. The material collection chamber may be located proximal or distal to the opening of the controllably arcuate segment, whereby the sliding member is retracted or advanced respectively to move the material received through the opening into the material collection chamber. In order to draw material from the outside of the catheter shaft through the opening in the controllably arcuate segment, a negative pressure or suction is applied at an opening on the proximal end of the catheter device. Aspiration or negative pressure may be maintained during the period of time that the sliding member is advanced or retracted. The present invention includes various means of providing the suction including connections to attach to syringes or sophisticated vacuum and material collection generators as well as integrated aspiration systems. The present invention may include one or more valves to prevent blood leakage, avoid over pressurization, allow one way flow of fluid and other material into or out of various chambers or other locations and other purposes.

In another preferred embodiment, the controllably arcuate segment has a normally bowed bias which is converted to a relatively straight geometric shape by integral straightening means. The normally bowed bias can be created during manufacturing with catheter shaping processes known to those of skill in the art, or with embedded curved stiffeners. The sliding member can function as the integral straightening means, as is described above, or an embedded element can change the controllably arcuate segment from a relatively bowed to a relatively straight geometry, on command, via controls located on the proximal portion of the device. In another preferred embodiment, the controllably arcuate segment has a normally straight bias which is converted to a relatively bowed geometric shape by integral curving means. Various curving means are described including mechanical pull wires or embedded curving elements that are attached, such as via electrical wires, to control means located on the handle on the proximal end of the device. An embedded battery and a switch located on the handle are used to connect the curving elements to a power source driving the shape change of the curving element. Multiple states, or transitional geometric shapes may be formed in the controllably arcuate segment in addition to a maximally straight and a maximally bowed geometry. Curving elements may be constructed of shaped memory components, such as shaped memory alloys or shaped memory polymers, piezo material, or electromagnet assemblies. Curving elements may have a filament shape, a tubular shape or a non-uniform shape. Curving elements may consist of single or multiple components that cause the controllably arcuate segment of the catheter shaft to transform to the proper bowed geometry, thus positioning the controllably arcuate segment's opening up against the wall of the body conduit into which the catheter device of the present invention is inserted. Curving or straightening elements may work in combination with a sliding member to change the geometry of the controllably arcuate segment. Changing curvature of the controllably arcuate segment can cause the openings in the segment to change shape including changing from a fluidly closed to a fluidly open state.

In a preferred embodiment, the proximal end of the catheter device includes a handle with an integrated plunger assembly. Retraction of a grasper moves a syringe like shaft and plunger to create a negative pressure at the opening in the controllably arcuate segment. In addition, continued retraction continues the aspirating pressures causing material to be drawn through one or more lumens in the catheter device to a chamber in the handle. Advancement of the grasper causes material to evacuate the chamber through a waste exit. In this particular embodiment, the grasper may also advance or withdraw a mechanical linkage connected to a sliding member which is used to sever or otherwise move material away from the opening in the controllably arcuate segment.

In a preferred embodiment, the catheter device includes a thru lumen from the proximal handle to the distal tip, such that material, such as thrombus, can be aspirated from the handle through the catheter shaft and removed from a location where the distal end of the catheter resides. Alternatively, a core assembly, such as an assembly including the mechanical linkage and sliding member, is removable wherein removal of the core creates the lumen that can be used to aspirate material from the distal end of the catheter. In another preferred embodiment, the catheter device includes a lumen for injecting fluids, such as radiopaque dye or blood thinning agents, wherein the lumen is attached to an input port on the handle of a the device and an exit located at or near the distal end of the catheter device. The lumen can also be used to extract material from the distal end of the catheter.

In another preferred embodiment, the catheter device includes an elongate catheter body with a proximal end and a distal end, an aspiration chamber located near the proximal end, a controllably arcuate segment including at least one opening, and an aspiration lumen in fluid communication with the aspiration chamber and one or more openings in the controllably arcuate segment. The device may include a sliding member to move material drawn through the opening under pressure, away from the opening. The device may have a normally bowed or a normally straight bias. The device may further include one or more curving elements, controllable from the proximal end of the catheter device, for transforming the controllably arcuate segment from one geometric shape to another.

A preferred method of using any of the catheter embodiments of the present invention is also disclosed. The method for removing material from a biological conduit includes providing a catheter device having an elongate catheter shaft having a proximal end and a distal end, a controllably arcuate segment including at least one opening in fluid communication with the proximal end and a sliding member that moves material received through the arcuate segment opening away from said opening. The device is percutaneously or surgically advanced into a biological conduit, preferably with the controllably arcuate segment in a relatively straight geometry, after which suction is applied to cause negative pressure at the one or more openings. The sliding member is then retracted to move material away from the opening. The controllably arcuate segment is changed to a relatively straight geometry prior to advancing, retracting or rotating the catheter device. In another preferred method, after the catheter device is used to first extract material, it is rotated and additional material is removed, each rotation accompanied by a predecessor step of changing to a relatively straight geometry, and each extraction step accompanied by a predecessor step of changing to a relatively bowed geometry.

Another preferred method is disclosed for removing material from a biological conduit comprising the steps of providing a catheter device having an elongate catheter shaft having a proximal end and a distal end, a controllably arcuate segment including at least one opening in fluid communication with the proximal end, percutaneously or surgically inserting and transluminally advancing the catheter into the biological conduit, applying suction to the at least one opening in the controllably arcuate segment and changing the shape of the controllably arcuate segment from a relatively bowed geometry to a relatively straight geometry. Additional steps may include changing from a relatively bowed to a relatively straight geometry prior to insertion of the catheter device. The device may be changed from a relatively straight geometry to a relatively bowed geometry prior to applying suction. Additional steps may include use of radiopaque markers to position the device within the body conduit.

The present invention, therefore, provides a catheter device for removing undesirable material, such as thrombus, from a body conduit, such as a saphenous vein graft or other blood vessel, including a controllably arcuate segment which further includes an opening that can be brought in contact with the undesired material with sufficient force such than under suction, the material is drawn through the opening into an lumen, cavity or chamber within the catheter device. The use of the device is simple and straightforward, and does not require bulky or expensive equipment not otherwise included in the various hospital settings in which it will be used.

These aspects of the invention together with additional features and advantages thereof may best be understood by reference to the following detailed descriptions and examples taken in connection with the accompanying illustrated drawings.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1A:
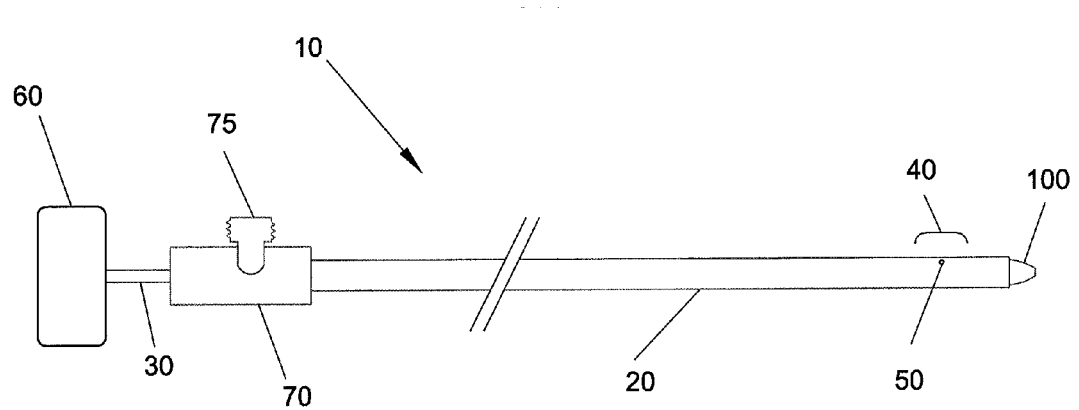
FIG. 1A is a side view of a first exemplary embodiment of a catheter device constructed in accordance with the present invention showing a controllably arcuate segment in a relatively straight geometry.
Figure 1B:
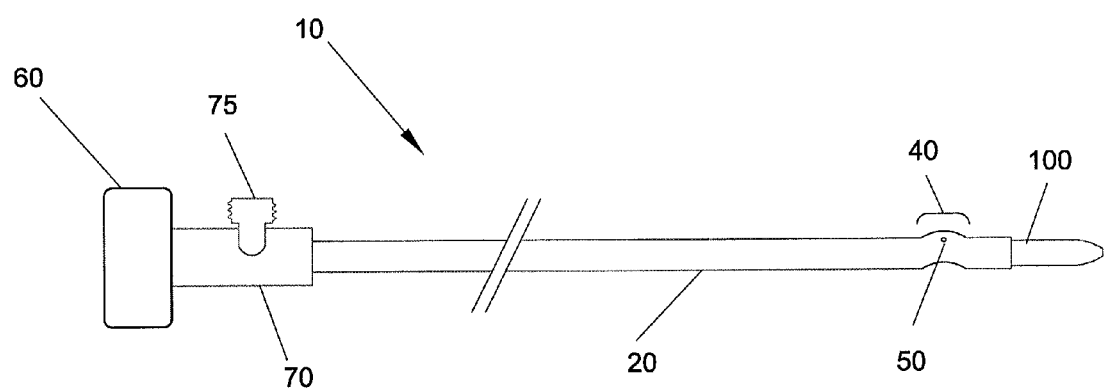
FIG. 1B is a side view of the device of FIG. 1A showing the controllably arcuate segment in a relatively bowed geometry.

Referring first to FIGS. 1A and 1B, there is illustrated an exemplary embodiment of a catheter device 10 constructed in accordance with the present invention. The catheter device 10 includes a catheter shaft 20 constructed of materials that are biocompatible and also permit flexibility of the device required to allow insertion into and advancement through the vasculature of a patient. Catheter shaft 20 contains one or more hollow lumens within its structure that allow flow of material such as blood or thrombus, as well as permit controlling shafts, mechanical linkages or flexible tubes or wires to slide back and forth. Fixedly attached to the proximal end of catheter shaft 20 is a handle, handle 70, which allows the user to advance and maintain the position of the distal end of catheter device 10, as well as rotate the catheter shaft 20.

Handle 20 includes aspiration port 75 that is in fluid communication with an internal lumen of catheter shaft 20. Aspiration port 75 can be connected to various means of creating a vacuum or suction, such as a vacuum generator or simple syringe. Aspiration port 75 may include standardized threads, such as standard luer threads, or other mechanical connection means to facilitate connection to the suction means, not shown. Aspiration port 75 is in fluid communication with a hollow lumen of catheter shaft 20 via a similar lumen, opening or cavity within handle 70, all not shown, but described in detail in subsequent figures. Exiting handle 70 is a mechanical linkage, linkage 30 which terminates at its proximal end with a separate handle for the user to grasp, grasper 60. Advancement and retraction of grasper 60 causes similar linear motion of linkage 30 that is slidingly received through the handle 70 and into catheter shaft 20.

Attached to the distal end of linkage 30 is a cylindrical element, sliding member 100. Preferably, both linkage 30 and sliding member 100 contain a thru lumen such that a standard interventional guidewire can be inserted therethrough, and catheter device 10 advanced and retracted over the guidewire using standard interventional over the wire techniques. The combined lengths of linkage 30 and sliding member 100 are preferably chosen such that when grasper 60 is in both a fully advanced and a fully retracted position, the distal tip of sliding member 100 exits the distal end of catheter shaft 20. Preferably, the distal end of sliding member 100 is tapered to allow atraumatic advancement of catheter device 10 through the vasculature or other body conduits.

Near the distal end of catheter shaft 20 is controllably arcuate segment 40, a finite length of shaft 20, proximal to the tip of catheter device 10, that can be controlled by the user to transform on command from a relatively straight geometry or shape, to a relatively bowed, or arcuate geometry. Included at or near the mid-portion of controllably arcuate segment 40 is a hole, opening 50, which traverses from the outer surface of shaft 20 to an internal cavity contained within shaft 20. Referring specifically to FIG. 1A, grasper 60 and sliding member 100 are shown in a retracted position, and the controllably arcuate segment 40 is shown in a relatively straight geometry. Referring now to FIG. 1B, grasper 60 and sliding member 100 are shown in a fully advanced position, and the controllably arcuate segment 40 is shown in a relatively bowed geometry. There are various means of achieving control of the shape of controllably arcuate segment 40 including embodiments in which the controllably arcuate segment 40 is normally bowed and means are provided for transforming to a relatively straight geometry, as well as embodiments in which the controllably arcuate segment 40 is normally straight, and means are provided for transforming to a relatively bowed geometry. Numerous means of controlling the shape of controllably arcuate segment 40 for FIGS. 1A and 1B as well as additional figures are described in detail herebelow.

FIGS. 1A and 1B depict a preferred embodiment in which a controllably arcuate segment 40 is simply a portion of catheter shaft 20 that has been formed or shaped in its manufacturing process to have a relatively bowed geometry. A common process for catheter shaping includes inserting a pre-shaped metal mandrel in the catheter during manufacture, and heating the device with the mandrel in place. The mandrel length and shape geometry would be designed to cause the proper bow at the proper location along the catheter shaft 20. After a cooling time, the mandrel is removed and the catheter assumes the desired shape. This process is often used to form complex catheter tip shapes common to various cardiovascular guide catheters, and is an effective way of shaping an elastomeric tube with one or more internal lumens. In FIGS. 1A and 1B, the sliding member 100 acts as the means of transforming the normally bowed controllably arcuate segment 40 from its manufactured bowed geometry to a relatively straight geometry. When the sliding member 100 is advanced beyond the length of the controllably arcuate segment 40, controllably arcuate segment 40 assumes its bowed configuration established during the manufacturing process. The material selection, thickness and other geometric parameters of sliding member 100 are chosen such that when grasper 60 is retracted, linkage 30 retracts sliding member 100 accordingly, causing a significant length of sliding member 100 to reside within the internal lumen of controllably arcuate segment 40, further causing controllably arcuate segment 40 to transform into a relatively straight geometry. When the grasper 60 and attached linkage 30 are advanced, the majority of length of sliding member 100 slides out of the internal lumen of controllably arcuate segment 40, allowing it to reassume its bowed geometry. Subsequent advancement and retraction of grasper 60, correspondingly advances and retracts linkage 30 and sliding member 100 such that controllably arcuate segment 40 transforms to a relatively bowed geometry to a relatively straight geometry respectively.

Referring again to FIGS. 1A and 1B, there is included near the midpoint of controllably arcuate segment 40 an hole, opening 50, which extends from the outer surface of catheter shaft 20 to an inner lumen. As described above, aspiration port 75 is in fluid communication with an internal lumen of catheter shaft 20, this particular lumen also in fluid communication with opening 50 such that when a vacuum is applied to aspiration port 75 by way of a syringe or other means, suction is applied at opening 50 causing material in close proximity to opening 50 to be drawn into the lumen of shaft 20 via opening 50. Controllably arcuate segment 40 construction materials and geometry and the geometry of opening 50 may be chosen such that when controllably arcuate segment 40 is in its relatively bowed geometry, opening 50 is relatively open, however when controllably arcuate segment 40 is in its relatively straight geometry, opening 50 is relatively closed.

Figure 2:
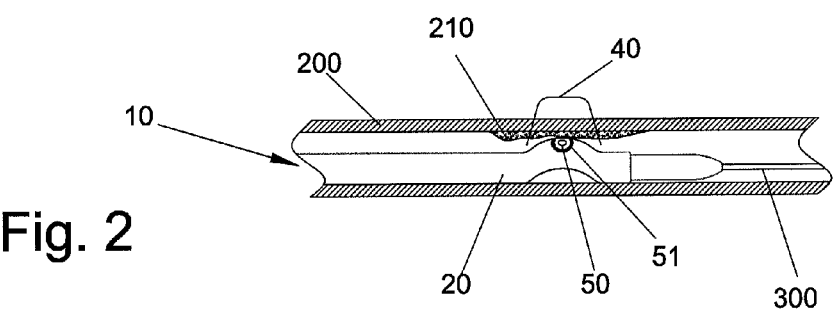
FIG. 2 is a cross-sectional view of the device of FIGS. 1A and 1B showing the opening in the controllably arcuate segment positioned at a site in a biological conduit prior to removal of occlusive material.

Referring now to FIG. 2, a preferred method of utilizing catheter device 10 is depicted. The catheter device 10 of the present invention can be placed percutaneously or intraoperatively, and advanced through a body conduit such as the vascular system. In a preferred embodiment, catheter device 10 is inserted percutaneously into the vasculature to treat a blood vessel, such as a coronary vessel or saphenous vein graft placed during coronary artery bypass graft surgery. Typically a guide catheter, not shown, is placed at a convenient vascular access point such as a femoral artery, and advanced to a point proximal to a stenotic location such as the ostium of an occluded saphenous vein graft. Typically a guidewire, such as an 0.014 inch guidewire, guidewire 300, is advanced through the guide catheter and into the lumen of the vessel to be treated to a location past the stenosis.

Next the catheter device 10 of the present invention is percutaneously inserted and transluminally advanced through the guide catheter and over guidewire 300 into the vessel to be treated, blood vessel 200, positioning the opening 50 of the controllably arcuate segment 40 near the area of occlusive material to be removed, occlusive material 210. Each time the catheter device 10 is inserted with the controllably arcuate segment 40 in the relatively straight geometric condition, shown in FIG. 2 at a later step with the controllably arcuate segment 40 in the relatively bowed geometry. The operator would assure and or change to that relatively straight geometry condition not only prior to insertion, but each time the device is transluminally advanced, withdrawn or rotated. In this particular embodiment, the catheter device of FIGS. 1A and 1B, the operator would simply retract grasper 60 to cause the controllably arcuate segment 40 to be in the relatively straight geometric shape. Other means for changing the shape of controllably arcuate segment 40 are described with the subsequent figures below. Catheter shaft 20 has a length appropriately chosen such that a small portion of the proximal end of catheter shaft 20 extends out of the guide catheter, placing handle 70 in close proximity to the insertion site, when opening 50 is properly positioned at the location of the occlusive material 210.

The axial position of the guide catheter, guidewire 300 and various components of catheter device 10 are known within the vessel utilizing conventional techniques and equipment which may include, for example, fluoroscopy, ultrasound, nuclear magnetic resonance imaging (NMR), and other visualization techniques and equipment commonly found in hospital operating rooms, catheterization laboratories and other therapeutic and diagnostic environments. In a preferred embodiment, catheter shaft 20 can be visualized with visualization equipment such as fluoroscopy, or catheter shaft 20 has been modified to be visualized. Insertion of radiopaque agents, such as barium sulfate, in small amounts, allows relatively thin catheter shafts to be visualized with x-ray equipment such as fluoroscopy. Various surface modification or air bubble impregnation techniques can be employed to make the implantable materials be visualized with ultrasound and other modifications can be accomplished to be compatible with other visualization technologies. Catheter shaft 20 and controllably arcuate segment 40 shall be modified such that the user can differentiate when the controllably arcuate segment 40 is in its relatively straight geometry versus its relatively bowed geometry. In a preferred embodiment, a visualization marker, marker 51, preferably a radiopaque band, is also included near or surrounding opening 50 such that during rotation of catheter shaft 20, the angular orientation as well as the longitudinal positioning of opening 50 can be visualized. Additionally, the catheter device 10 may include an internal lumen or pathway, not shown, that allows angiographic dye to be injected into it, exiting at a point at or near the distal tip of catheter shaft 20, such as through the guidewire lumen, around the guidewire lumen, or through opening 50.

Referring still to FIG. 2, the catheter device 10 has been transluminally advanced over guidewire 300 such that opening 50 has been positioned near the occlusive material 210. Note that at this point in the procedure, controllably arcuate segment 40 remains in the relatively straight geometry, not depicted in FIG. 2, that it has maintained through the entire insertion process thus far. At this time, the operator transforms the controllably arcuate segment 40 from the relatively straight geometry to the relatively bowed geometry depicted in FIG. 2. With the particular embodiment of FIGS. 1A and 1B, the operator would simply advance the grasper 60 to its fully advanced position. The outside diameter of catheter shaft 20 is chosen to be somewhat less than the inner diameter of the vessels it is advanced through, including the vessel diameter at the stenosis. The radius of curvature and length of controllably arcuate segment 40 in its maximally bowed geometric shape is chosen such that opening 50 is pushed against the occlusive material with some amount of force. Catheter device 10 will be manufactured with not only various lengths and diameter profiles, but numerous radii of curvature and segment lengths for controllably arcuate segment 40, to accommodate a range of body conduits to be treated, specifically blood vessels such as saphenous vein grafts. Catheter diameters, lengths and other geometric criteria are chosen based on the path from the percutaneous entry site to the treatment site, as well as the size and geometry of the vessel to be treated and the size and geometry of the occlusive material to be removed. In its maximally bowed geometry depicted in FIG. 2, the opening 50 of controllably arcuate segment 40 is positioned such that as suction is applied via aspiration port 75, occlusive material 210 is drawn into an internal cavity of catheter shaft 20. In a preferred embodiment, controllably arcuate segment 40 at the general area of opening 50 would place a small amount of force against the occlusive material when the controllably arcuate segment 40 is in its relatively bowed geometric shape.

A next step for the operator is to retract grasper 60 causing linkage 30 and thus sliding member 100 to also retract. As sliding member 100 retracts, its proximal end pushes, potentially cutting, material projecting through opening 50 to a location away from the opening, more proximal to the aspiration port 75. Vacuum or suction may be maintained during the retraction of sliding member 100. Optionally, grasper 60 can be advanced again, advancing linkage 30 and sliding member 100 causing controllably arcuate segment 40 to change from a relatively straight geometry to a relatively bowed geometry and positioning opening 50 again against any remaining occlusive material 210. Suction can be reapplied, and grasper 60 again retracted, once again moving any material protruding through opening 50 away from opening 50, as well as causing controllably arcuate segment 40 to change from a relatively bowed geometry to a relatively straight geometry.

When the controllably arcuate segment 40 has been placed in its relatively straight geometry, the catheter device 10 can be removed by retracting it back over guidewire 300 and out through the guide catheter leaving guidewire 300 and the guide catheter in place. Alternatively, also when the controllably arcuate segment 40 has been placed in its relatively straight geometry, the handle 70 can be rotated causing catheter shaft 20 to also rotate. When opening 50 is rotated to its desired angular position, as may be determined using fluoroscopy and marker 51, grasper 60 can be advanced, again causing controllably arcuate segment 40 to change to its relatively bowed condition and simultaneously positioning opening 50 with a minimal level of force against additional occlusive material. Suction can again be applied, causing additional material to be drawn through opening 50, and grasper 60 can then be retracted, causing linkage 30 and thus sliding member 100 to simultaneously retract similarly pushing the additional material protruding through opening 50 away from opening 50 as well as causing controllably arcuate segment 40 to change from a relatively bowed geometry to a relatively straight geometry.

A preferred method includes the steps of 1) changing controllably arcuate segment 40 to its relatively bowed shape; 2) applying suction; 3) retracting grasper 60 and thus also retracting sliding member 100; 4) advancing grasper 60 and thus also advancing sliding member 100 simultaneously causing controllably arcuate segment 40 to change back to a relatively straight geometry and 5) rotating handle 70 and thus catheter shaft 20. These steps can be repeated through a 360 degree rotation or more to remove undesired material present along the luminal walls of a body conduit. In addition to the above steps, longitudinal positioning, forward or back, may also be performed, again only with the controllably arcuate segment 40 in its relatively straight geometric condition. It should be noted that it might not be necessary to change the controllably arcuate segment 40 from a bowed condition to a maximally straight geometry for some forms of repositioning such as rotation or transluminal advancement or retraction. Partial straightening may suffice. Also, the above description include two distinct shapes for controllably arcuate segment 40, it should be noted that modifications to the controlling means, such as grasper 60, linkage 30 and sliding member 100 described hereabove, can be made to allow the operator to place controllably arcuate segment 40 in multiple transitional shapes from a maximally bowed geometry to a maximally straight geometry.

Although this system was described specifically for a saphenous vein graft, it is readily applicable to any stenosis of a vessel or other applicable tubular conduit in the body. For example, the catheter device 10 could be used to open stenoses in the other coronary vessels, a carotid artery, dialysis fistulas, peripheral vasculature, etc. Although the present invention has only been described for the removal of plaque or thrombus, the catheter device 10 could also be used to remove other stenotic or occluding material or tissue from ducts such as the ureters or the fallopian tubes. Mammalian patients would include both humans and other animal patients.

Figure 3:
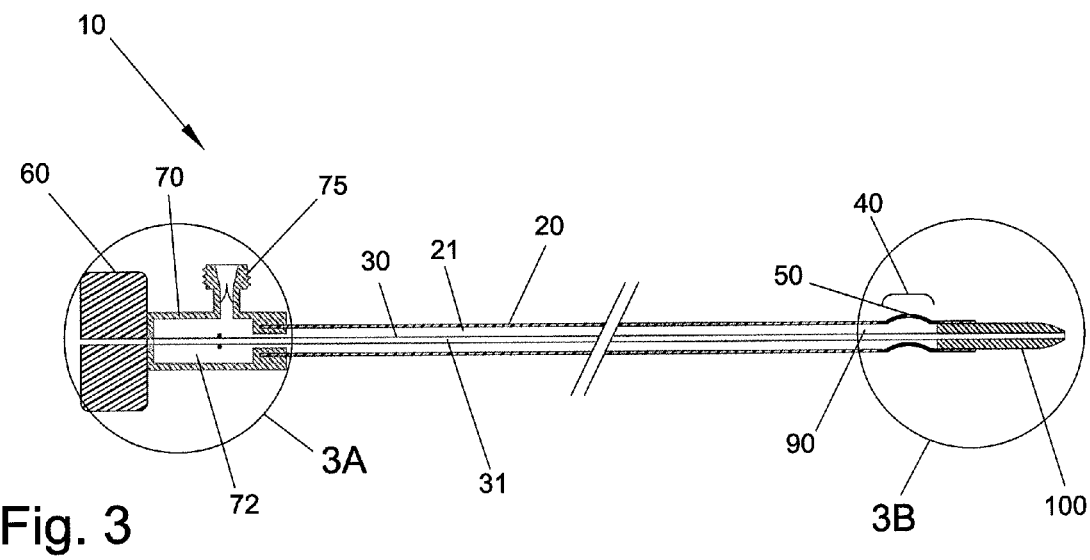
FIG. 3 is a cross-sectional view of a preferred embodiment of a catheter device constructed in accordance with the present invention.
Figures 3A, 3B:
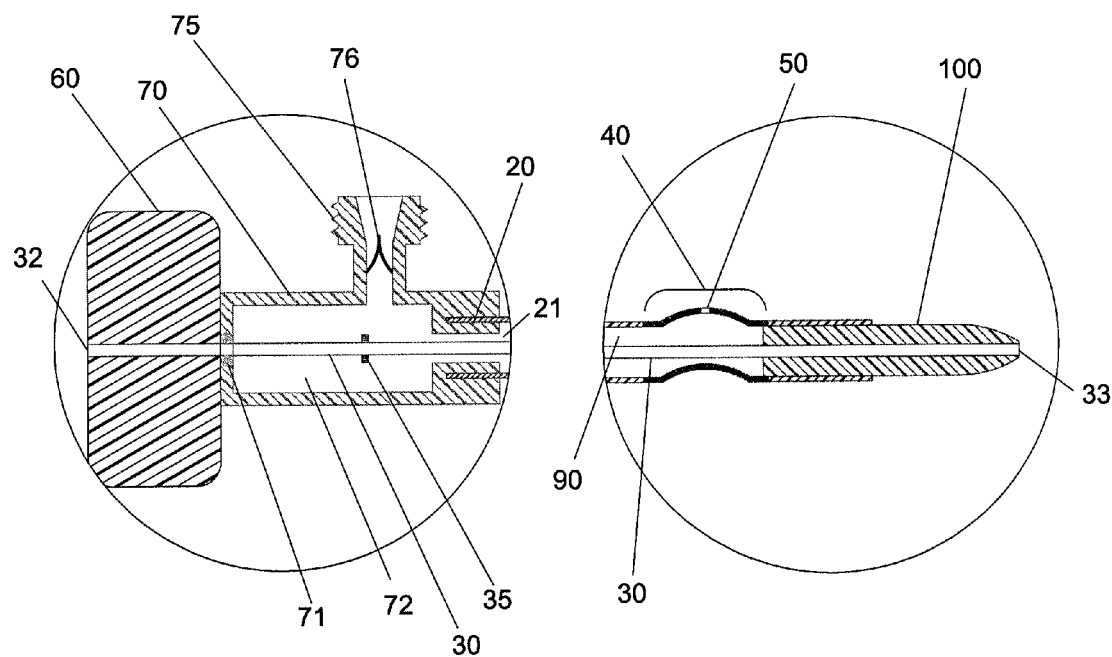
FIG. 3A is an enlarged sectional view of the proximal end of the catheter device contained in circle 3A of FIG. 3.
FIG. 3B is an enlarged sectional view of a distal end of the catheter device contained in circle 3B of FIG. 3.

FIGS. 3, 3A and 3B show another preferred embodiment of catheter device 10 which is similar to the catheter device of FIGS. 1A and 1B with grasper 60, linkage 30 and sliding member 100 all in a fully advanced position and controllably arcuate segment 40 in its maximally bowed geometry. Accordingly, elements of this embodiment which are similar to elements of catheter device 10 of FIGS. 1A and 1B are referenced with the same reference numerals. Referring specifically to FIG. 3, catheter device 10 includes an aspiration chamber 72 included in handle 70. Catheter shaft 20 is fixedly attached to handle 70 while creating a fluid path from aspiration port 75, into aspiration chamber 72 and continuing through aspiration lumen 21 to material collection chamber 90. Material collection chamber 90 is in fluid communication with opening 50 of controllably arcuate segment 40. As shown in FIG. 3, material collection chamber 90 may be a simple continuation of aspiration lumen 21, or material collection chamber 90 may have a specific geometry or cavity-like structure while still in fluid communication with aspiration lumen 21.

Present within an internal lumen of catheter shaft 20 is a flexible shaft, linkage 30, which is preferably a hollow tube permitting a guidewire to be inserted through its internal lumen, linkage lumen 31. Linkage 30 may be constructed of a flexible metal, such as a flexible steel hypotube, or a superelastic material such as Nitinol, a nickel titanium alloy in its superelastic state. Alternatively, linkage 30 may be constructed of a flexible plastic tube. As shown in FIGS. 3 and 3A, an opening around linkage 30 provides fluid communication between aspiration chamber 72 and aspiration lumen 21. At its proximal end, linkage 30 is fixed to grasper 60 that controls the advancement and retraction of linkage 30 and its connected components. Linkage 30 is fixed at its distal end to sliding member 100. The grasper 60, linkage 30 and sliding member 100 are shown in the fully advanced position and the controllably arcuate segment 40 is shown in a maximally bowed geometry.

Referring additionally to FIG. 3A, grasper 60 surrounds and is fixedly attached to linkage 30. The proximal end of linkage 30 includes guidewire opening 32 into which a guidewire can be placed and from which a guidewire can exit. Linkage lumen 31 may include a valve, not shown, in its path to prevent leakage of blood once inserted. Alternatively, the diameter of linkage lumen 31 is chosen to be as small as possible, slightly larger than the outside diameter of the guidewire it is to be placed over. Linkage 30 enters handle 70 such that a relatively fluid tight seal is created. In order to prevent fluid leakage, a sealing element, linkage seal 71, is included that preferably consists of an elastomeric o-ring which seals between handle 70 and linkage 30 yet allows linkage 30 to slide back and forth as grasper 60 is advanced and retracted. Linkage 30 may include a mechanical stop, such as linkage stop 35, included on the outer diameter of linkage 30 to limit the maximum retraction distance of grasper 60. Linkage stop 35 is positioned along the outer diameter of linkage 30 such that when grasper 60 is retracted, linkage stop 35 makes contact with the inside surface of aspiration chamber 72 and linkage seal 71 limiting further retraction. At this maximally retracted state, shown in FIGS. 4, 4A and 4B, sliding member 100 is positioned within controllably arcuate segment 40.

As shown in FIG. 3A, aspiration port 75 may include a valve, connector valve 76, such that when the attachable vacuum source, such as a vacuum generator or syringe, is not attached, fluid will not leak out of aspiration chamber 72. Aspiration lumen 21 is in fluid communication with aspiration chamber 72 through a clearance around linkage 30 and an opening in the distal end of handle 70 inside of the attachment point for catheter shaft 20.

Referring additionally to FIG. 3B, Sliding member 100 includes a thru lumen continuing the guidewire clearance lumen provided by linkage 30. At the distal end of sliding member 100 is guidewire exit 33, which allows the guidewire to be inserted into or exit from the device during over the wire procedures. FIGS. 3, 3A and 3B show grasper 60 in its fully advanced position, and FIG. 3b depicts the corresponding location of sliding member 100 in its fully forward or advanced position with controllably arcuate segment 40 shown in its maximally bowed geometry. Located at the midpoint of controllably arcuate segment 40 is opening 50 that creates a fluid path from the outer portion of controllably arcuate segment 40 to material collection chamber 90. Opening 50 is sized to allow collection of occlusive material, such as thrombus, utilizing various applicable vacuum pressures. Opening 50 may be a single hole or multiple holes, the holes may be round, oval or other shape. The holes may be of uniform geometry from inside to outside, or the holes may be tapered or transform in shape as they pass through the wall of controllably arcuate segment 40. Furthermore, opening 50 may be designed such that an open fluid path is created only when controllably arcuate segment 40 is in a relatively bowed geometry and the fluid path through opening 50 is closed or near closed when controllably arcuate segment 40 is in a relatively straight geometry.

In a preferred embodiment, controllably arcuate segment 40 is normally bowed and is transformed to a relatively straight geometry when sliding member 100 is retracted to reside within the lumen of controllably arcuate segment 40. Controllably arcuate segment 40 can be normally bowed by a treatment, such as a heat treatment, in the manufacturing process as has been described hereabove, via embedded curving elements in or near the controllably arcuate segment 40 or via other curving means. Various designs for curving elements can be provided such as internal curving or bending members, the details of which are described in subsequent embodiments in detail hereinbelow.

Figure 4:
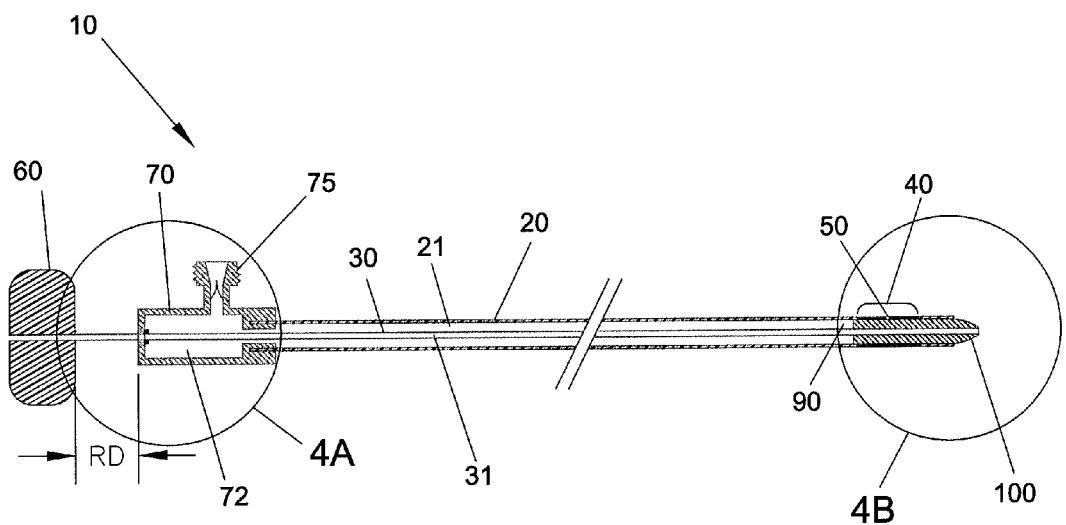
FIG. 4 is a cross-sectional view of the catheter device of FIG. 3 shown with a grasper of the handle assembly in a retracted position.
Figures 4A, 4B:
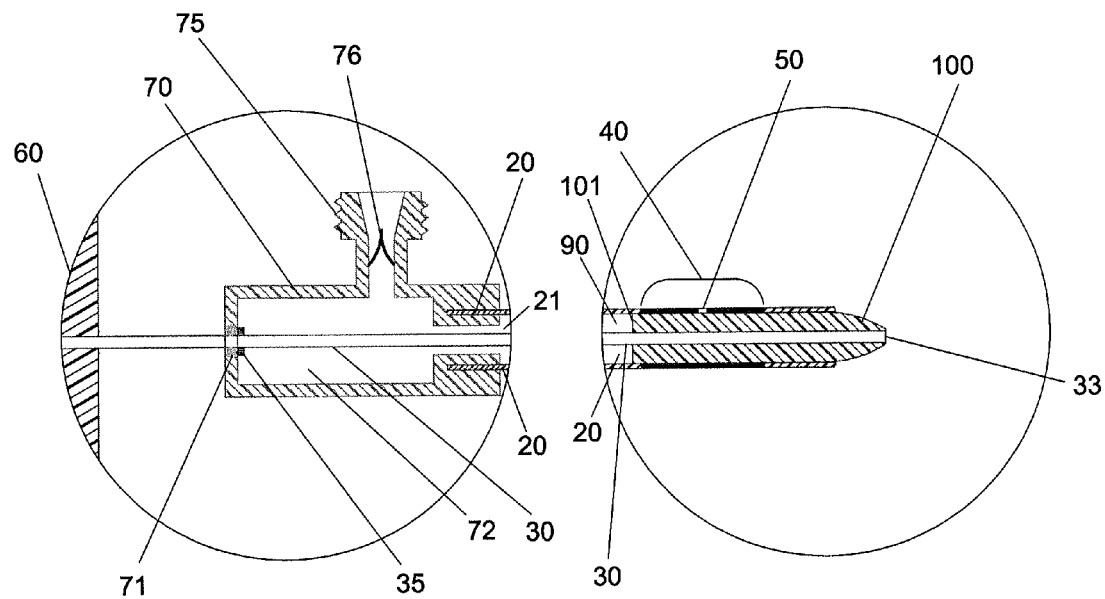
FIG. 4A is an enlarged sectional view of the proximal end of the catheter device contained in circle 4A of FIG. 4.
FIG. 4B is an enlarged sectional view of the distal end of the catheter device contained in circle 4B of FIG. 4.

FIGS. 4, 4A and 4B show the catheter device 10 of FIGS. 3, 3A and 3B with grasper 60, linkage 30 and sliding member 100 all in a fully retracted position and controllably arcuate segment 40 in its maximally straight geometry. Accordingly, elements of this embodiment which are similar to elements of catheter device 10 of FIGS. 3, 3A and 3B are referenced with the same reference numerals. Referring specifically to FIG. 4, grasper 60 has been pulled back from its advanced position a distance equal to retraction distance RD. Accordingly, linkage 30 and sliding member 100 have also traveled in a direction toward the proximal end and away from the distal end of catheter device 10 an equivalent distance equal to retraction distance RD. Referring additionally to FIG. 4A, the amount of retraction distance is limited by a radial projection, linkage stop 35, which is fixedly attached to linkage 30 and stops further retraction when linkage stop 35 contacts linkage seal 71 and or the proximal end of aspiration chamber 72. Referring additionally to FIG. 4B, sliding member 100, in its fully retracted position, has its proximal portion fully contained within an internal lumen of controllably arcuate segment 40 causing controllably arcuate segment 40, which is naturally biased to be in a relatively bowed geometry, to be transformed into a relatively straight geometry. Sliding member 100 may be made from a material more rigid than the material of catheter shaft 20, such as a metal or a more rigid plastic or elastomer, and or its geometric construction chosen such that controllably arcuate segment 40 is straightened by the straight sliding member 100 in its fully retracted position. Sliding member 100 preferably includes a thru lumen with an exit, guidewire exit 33, that is coaxial with a linkage lumen 31 which is a thru lumen of linkage 30.

As grasper 60 is withdrawn from its fully advanced position, as shown in FIGS. 3, 3A and 3B, to its fully retracted position, as shown in FIGS. 4, 4A and 4B, the proximal end, cutting end 101 of sliding member 100 retracts toward and reaches opening 50 of controllably arcuate segment 40. With suction applied at aspiration port 75 and communicated to opening 50 via aspiration lumen 21 and material collection chamber 90, loose material near the outside surface of catheter shaft 20 in the region of opening 50 will be pulled through opening 50 to the inside of catheter shaft 20. As grasper 60 is continually retracted, and sliding member 100 continues to retract past opening 50, the material pulled through opening 50 by the suction is cut and or pushed by sliding member 100 away from opening 50 further into material collection chamber 90. Simultaneous with the retraction of sliding member 100 is the transformation of controllably arcuate segment 40 from a relatively bowed geometry to a relatively straight geometry. FIGS. 3 and 3B and FIGS. 4 and 4B show a controllably arcuate segment 40 with a symmetrical geometry, specifically wherein opening 50 is at the midpoint of the semicircle of controllably arcuate segment 40 and the two arcs on either side of opening 50 have the same radius of curvature and length. It should be appreciated, and considered within the scope of this application, that various other non-symmetrical geometries are applicable, and may be preferred, such as a geometry wherein the controllably arcuate segment 40 has been minimally straightened when sliding member 100 reaches opening 50 and the majority of straightening of controllably arcuate segment 40 occurs when sliding member 100 is further retracted to the maximum retraction of grasper 60.

Opening 50 is covered and may be sealed by sliding member 100 when grasper 60, linkage 30 and sliding member 100 are in their fully retracted position as is limited by linkage stop 35 and sliding member 100 has its proximal portion contained within controllably arcuate segment 40. Continued application of vacuum or aspiration at aspiration port 75 for the purpose of evacuating the material severed by cutting end 101 of sliding member 100 and contained in material collection chamber 90 may best be accomplished with inclusion of an additional thru lumen, not shown, to aspiration lumen 21 such that a circulatory path is provided to properly flush out the material from collection chamber 90 through aspiration lumen 21 and into aspiration chamber 72 where it can then be evacuated into the vacuum source connected to aspiration port 75. Note that in FIGS. 3, 3A, 3B, 4, 4A and 4B aspiration lumen 21 and material collection chamber 90 are a continuous cross-section lumen with material collection chamber 90 simply the part of that lumen closest to opening 50 of controllably arcuate segment 40. It should be understood, and it may be desirable, for material collection chamber 90 to have a larger cross sectional area than aspiration lumen 71, or to have other alternative shapes to facilitate the collection of body material that is pushed into material collection chamber 90 each time 1) vacuum is applied to aspiration port 75 with opening 50 positioned at a target stenotic location of a vessel; 2) controllably arcuate segment 40 is in a relatively bowed geometry; and 3) sliding member 100 is retracted.

Figure 5:
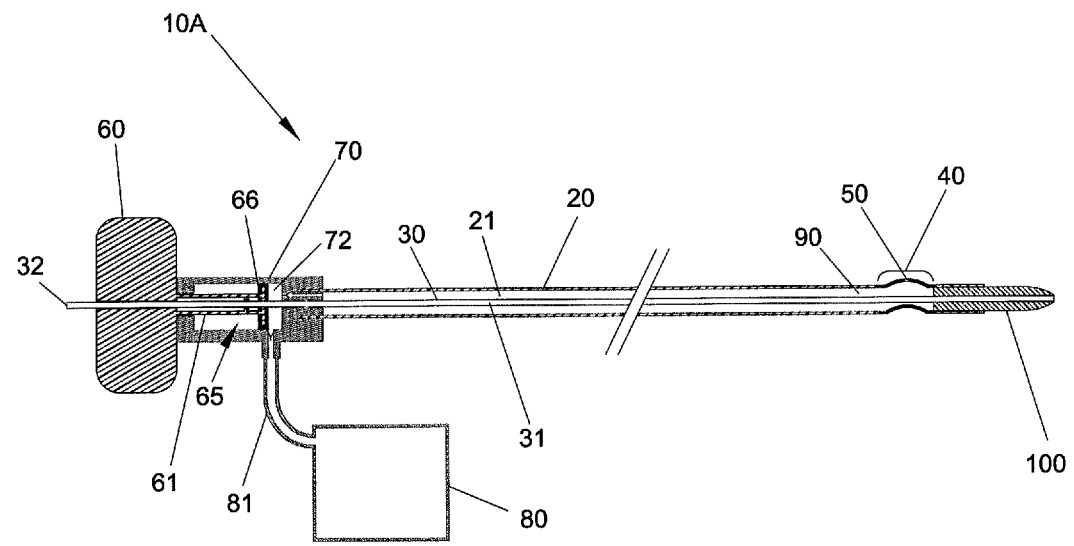
FIG. 5 is a cross-sectional view of another preferred embodiment of a catheter device constructed in accordance with the present invention.

FIGS. 5 and 5A thru 5G show another preferred embodiment of the catheter device of the present invention which is similar to the catheter device 10 of FIGS. 1A and 1B further comprising an integral aspiration or vacuum assembly and a connected waste receptacle. Accordingly, elements of this embodiment which are similar to elements of catheter device 10 of FIGS. 1A and 1B are referenced with the same reference numerals. Referring specifically to FIG. 5, catheter device 10A includes a catheter shaft 20 which is fixedly attached to handle 70 and includes one or more lumens extending from the proximal end to a point at or near the distal end, and may additionally include enclosed cavities or chambers which may be used to store collected occlusive material. A chamber within handle 70, aspiration chamber 72 includes a syringe-like piston and plunger, plunger assembly 65. A flexible linkage, linkage 30, exits the proximal end of handle 70 and continues through an internal lumen of catheter shaft 20 and is connected at its distal end to sliding member 100, shown in FIG. 5 in its fully advanced position. Linkage 30 contains a lumen therethrough, linkage lumen 31, which is sized to fit over a standard guidewire, such as an 0.014 guidewire. Linkage lumen 31 includes an opening at its proximal end, guidewire opening 32.

Controllably arcuate segment 40, shown in its maximally bowed geometry, is again showed with a normally curved bias which can be caused by numerous means such as those described in detail hereabove and herebelow. Alternatively, controllably arcuate segment 40 may have a normally straight bias, with shape control means changing controllably arcuate segment 40 to a bowed bias as is shown and described in detail in subsequent figures and their detailed descriptions provided herebelow. Controllably arcuate segment 40 has, near its midsection, an opening 50 which traverses from the outside surface of controllably arcuate segment 40 to an internal lumen in fluid communication with a chamber, material collection chamber 90, used to store previously occlusive material, such as thrombus, which has been drawn via suction through opening 50 when the controllably arcuate segment 40 is in a relatively bowed geometry. Material collection chamber 90 is shown in fluid communication with a lumen of catheter shaft 20, aspiration lumen 21, which is in fluid communication with aspiration chamber 72.

Alternatively, not shown, material collection chamber 90 may be a captured cavity, in fluid communication with opening 50 only, sized to store an appropriate amount of extracted occlusive material. In this particular embodiment, aspiration lumen 21 would be fluidly connected to opening 50 to permit aspiration, or an applied vacuum, to opening 50 to draw the occlusive material through opening 50, and may include a valve, such as a flap valve, also not shown, to isolate aspiration lumen 21 from opening 50 and or material collection chamber 90 when a suction is not applied via aspiration lumen 21. Such a valve would prevent collected material from being drawn into the aspiration lumen 21 from the material collection chamber 90 when suction is applied to aspiration lumen 21. Similar to previous embodiments, when sliding member 100 is withdrawn, the protruding occlusive material would be pushed into the closed cavity material collection chamber 90.

Figure 5A:
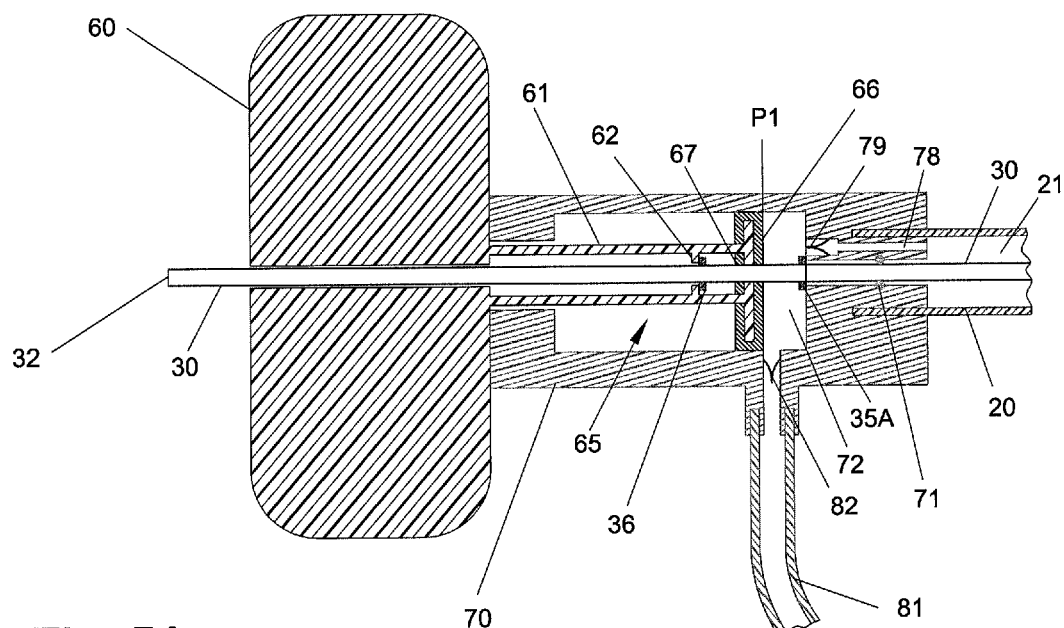
FIG. 5A is an enlarged sectional view of the proximal end of the catheter device of FIG. 5 shown with the grasper of the handle assembly shown in a fully advanced position.

Still referring to FIG. 5, aspiration chamber 72 has an attached evacuation chamber, waste chamber 80, connected to aspiration chamber 72 via waste exit 81. Referring additionally to FIG. 5A, plunger assembly 65 includes a longitudinal shaft, plunger shaft 61 which is fixedly connected on its proximal end to grasper 60 and includes on its distal end a flexible covering, plunger 66, which forms a seal with the inner walls of aspiration chamber 72. Preferably, aspiration chamber 72 has a circular cross section, however other cross sections are viable including oval, rectangular as well as asymmetrical cross sections. The cross section of aspiration chamber 72 is uniform along, at a minimum, the length of travel of plunger assembly 65 in which plunger 66 contacts the inner walls of aspiration chamber 72. Plunger shaft 61 is made from a rigid material such as a rigid plastic commonly used in standard syringes, and the distal end of plunger shaft 61 has a shape approximating the shape of the cross-section of aspiration chamber 72. Plunger 66 covers the distal end of plunger shaft 61 and is preferably made of a flexible material such as rubber or other material with properties to facilitate a fluid seal between the plunger assembly 65 and the walls of aspiration chamber 72. Plunger 66 is shown as a covering for a disk-like projecting end of plunger shaft 61 but it should be understood that various other geometries could be utilized to form the desired seal including a simple notch along the outer diameter of plunger shaft 61 wherein plunger 66 is a standard O-ring.

As shown specifically in FIG. 5A, catheter shaft 20, preferably of circular cross section, is mechanically attached to handle 70. Aspiration lumen 21 is in fluid communication with an internal cavity of handle 70, aspiration chamber 72 via handle aspiration lumen 78. Handle aspiration lumen 78 may include a one way valve, such as a duck-bill valve, aspiration valve 79 shown. Aspiration valve 79 allows fluid and material to pass from material collection chamber 90 and aspiration lumen 21 into aspiration chamber 72 when negative pressure or suction is applied within aspiration chamber 72 however prevents material from entering aspiration lumen 21 when positive pressure is applied within aspiration chamber 72. Negative pressure is created when plunger assembly 65 is retracted by the operator, and positive pressure is created when plunger assembly 65 is advanced. When positive pressure is created, liquid and material collected in aspiration chamber 72 exits to waste chamber 80 via waste exit 81. Waste chamber 80 may be a rigid or preferably flexible container such as a flexible bag or pouch. Waste exit 81 may be a piece of tubing, attached to handle 70 to cause a fluid path to aspiration chamber 72. Waste exit 81 may include an integrated one way valve, waste valve 82, such as a duck-bill valve similar in construction and performance to aspiration valve 79. When plunger assembly 65 is advanced by advancing grasper 60, the positive pressure created drives the liquid and other material from aspiration chamber 72 into waste exit 81 and eventually waste chamber 80. Waste chamber 80 may include a vent, not shown.

Plunger shaft 61 includes a lumen therethrough, which provides some clearance around linkage 30. Plunger shaft 61 further includes a projection, shaft projection 62, extending radially inward from plunger shaft 61 while making minimal or no contact with the outer surface of linkage 30. Linkage 30 includes a projection, linkage projection 36 extending radially outward from linkage 30 while making minimal or no contact with the inner surface of plunger shaft 61. The projections, linkage projection 36 and shaft projection 62 are positioned to cause a specific series of coordinated and timed linear movements of linkage 30 and sliding member 100 as grasper 60 and connected plunger assembly 65 are advanced and retracted by the operator. The linear movements are described in detail herebelow with reference to FIGS. 5A thru 5G. As shown in FIGS. 5 and 5A, grasper 60 and plunger assembly 65 is shown in its maximally advanced positioned, advanced position P1. Linkage 30 and sliding member 100 are also in their maximally advanced position as caused by shaft projection 62 forcing linkage projection 36 forward. Plunger 66 has a surface, proximal edge 67, which faces linkage projection 36 and when plunger assembly 65 is in advanced position P1, proximal edge 67 is offset from linkage projection 36. Grasper 60 is maximally advanced when it makes contact with handle 70. Linkage 30 may include another projection, linkage stop 35A, to limit advancement of linkage 30. Linkage stop 35A also extends radially outward and positioned along linkage 30 to limit forward travel by making contact with the distal end of aspiration chamber 72. Each of the projections, linkage stop 35A, linkage projection 36 and shaft projection 62 may have a ring-like structure fully surrounding their appropriate shafts or may be one or more rectangular projections.

Figure 5B:
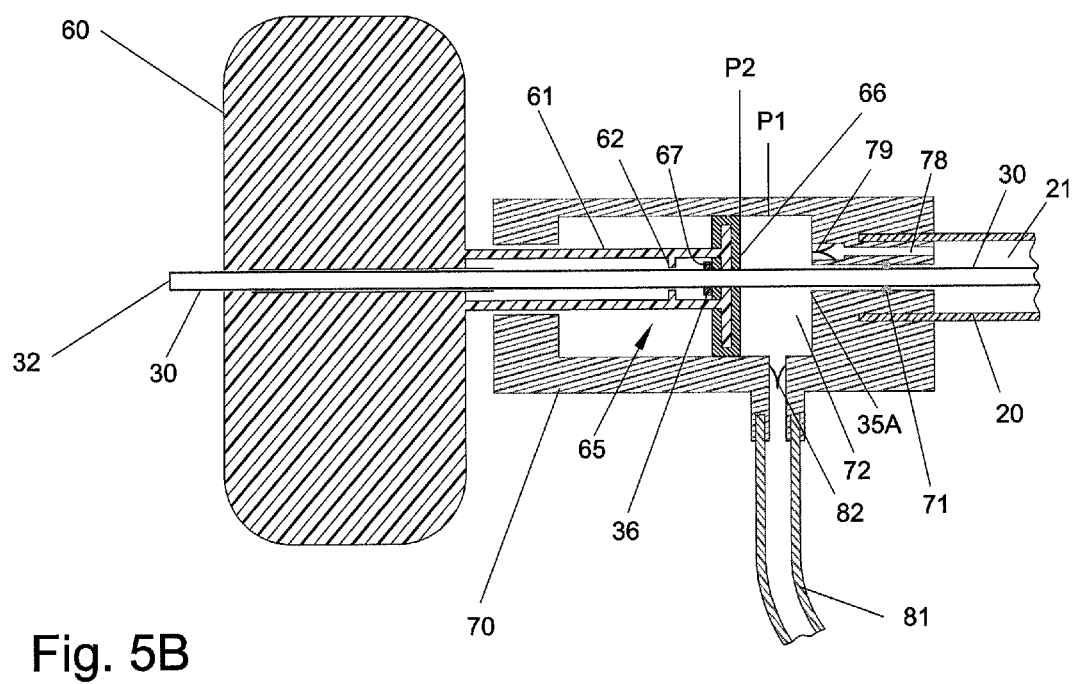
FIG. 5B is an enlarged sectional view of the proximal end of the catheter device of FIG. 5 shown with the grasper of the handle assembly shown in a partially retracted position.
Figure 5C:
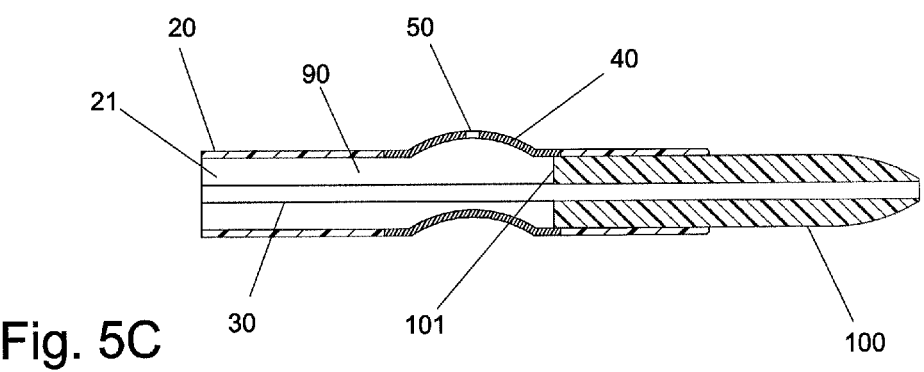
FIG. 5C is an enlarged sectional view of the distal end of the catheter device of FIG. 5 shown with the sliding member in the partially retracted position corresponding to the grasper position of FIG. 5B.

Referring now to FIGS. 5B and 5C, Grasper 60 has been partially retracting causing partial retraction of plunger assembly 65 to intermediate position P2. During retraction, negative pressure is created in aspiration chamber 72 and this suction is communicated from aspiration chamber 72 through handle aspiration lumen 78 and its internal valve, aspiration valve 79, into aspiration lumen 21, through material collection chamber 90 to opening 50. Fluid communication, in other words the effect of the negative pressure, is cut off from waste exit 81 by the action of waste valve 82 oriented to prevent flow from waste exit 81 into aspiration chamber 72. Since proximal edge 67 has just made contact with linkage projection 36, movement of plunger assembly 65 from advanced position P1 to intermediate position P2 has not caused any retraction of linkage 30, therefore sliding member 100 has not moved, and controllably arcuate segment 40 remains in its bowed geometry. When appropriately placed in a blood vessel for material extraction, relatively loose material, such as thrombus, in the general proximity to opening 50 would be drawn through opening 50. It should be appreciated and understood that configurations in which aspiration lumen 21 communicates directly with opening 50 not by way of material collection chamber 90, configurations not shown, could be used and is another preferred embodiment of this application.

Figure 5D:
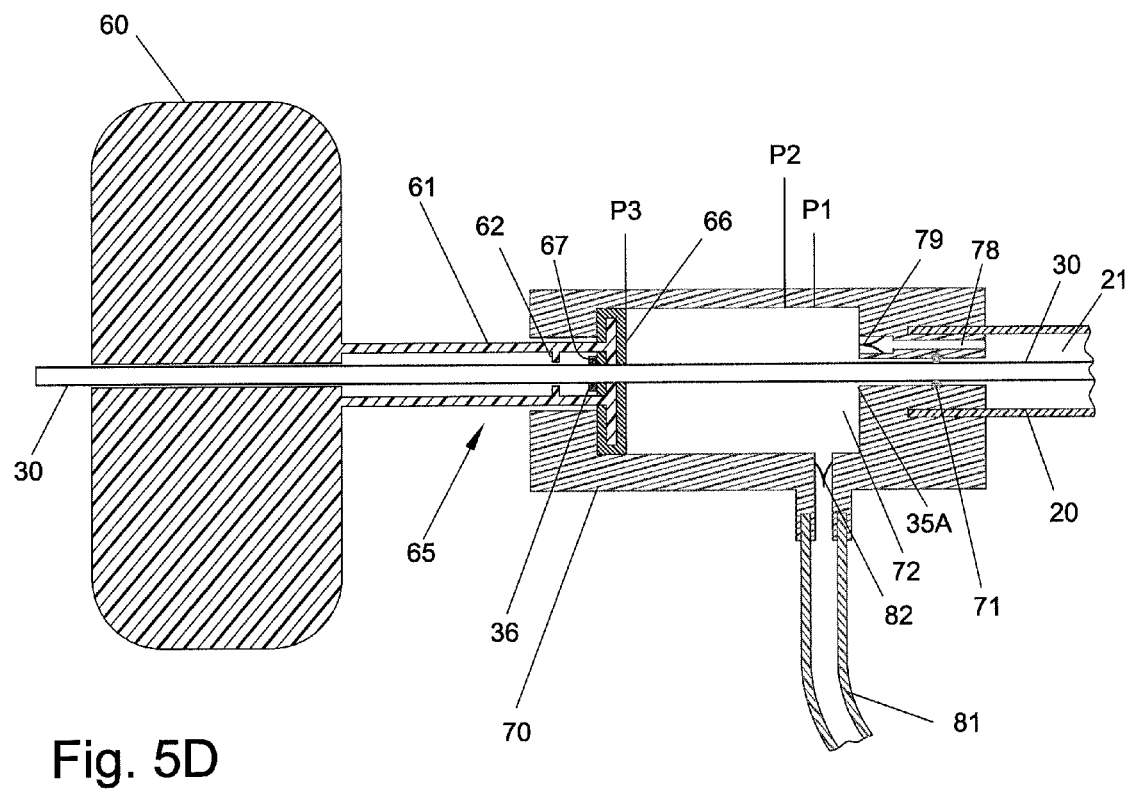
FIG. 5D is an enlarged sectional view of the proximal end of the catheter device of FIG. 5 shown with the grasper of the handle assembly shown in a fully retracted position.
Figure 5E:
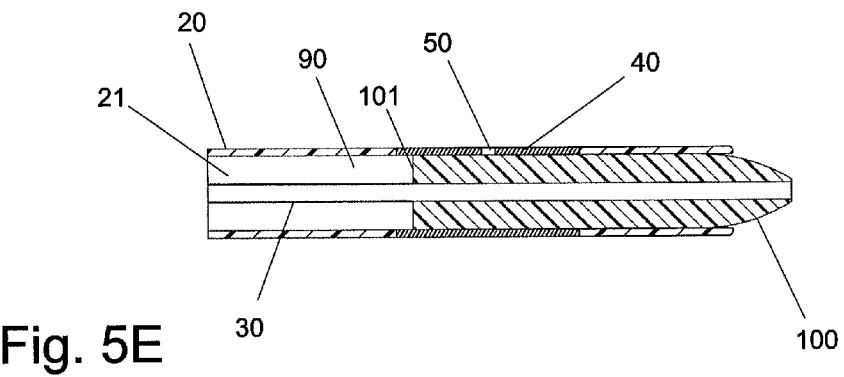
FIG. 5E is an enlarged sectional view of the distal end of the catheter device of FIG. 5 shown with the sliding member in the fully retracted position corresponding to the grasper position of FIG. 5D.

Referring now to FIGS. 5D and 5E, Grasper 60 has been fully retracting causing full retraction of plunger assembly 65 to retracted position P3. During retraction, negative pressure continued to be created in aspiration chamber 72 and this suction is communicated from aspiration chamber 72 through handle aspiration lumen 78 and its internal valve, aspiration valve 79, into aspiration lumen 21, through material collection chamber 90 to opening 50, similar to the suction created as plunger assembly 65 retracts from advanced position P1 to intermediate position P2. Fluid communication, in other words the effect of the negative pressure, remains to be cut off from waste exit 81 by the action of waste valve 82 oriented to prevent flow from waste exit 81 into aspiration chamber 72. Movement of plunger assembly 65 from intermediate position P2 to retracted position P3 has now caused linkage 30 to also retract, caused by an urging force generated by proximal edge 67 of plunger 66 pushing on linkage projection 36 of linkage 30, simultaneously causing sliding member 100, fixedly attached to the end of linkage 30, to also retract. The retraction of sliding member 100 is such that the proximal longitudinal portion of sliding member 100 resides within controllably arcuate segment 40 and sliding member 100 is of sufficient rigidity to cause controllably arcuate segment 40 to transition from its normally biased curved geometry to the relatively straight geometry of sliding member 100. The material that was previously drawn via suction through opening 50 is pushed away from opening 50 into material collection chamber 90 as the sliding member 100 is retracted by plunger assembly 65 moving from intermediate position P2 to retracted position P3.

With grasper 60 in the fully retracted position, as represented in FIGS. 5D and 5E, plunger assembly 65 as well as sliding member 100 are also retracted and controllably arcuate segment 40 is in a relatively straight geometry. In this state, the catheter device 10A could be removed from patient's body and the procedure completed. Alternatively, additional steps of an alternative procedure may be performed wherein additional one or more cycles of changing controllably arcuate segment 40 from straight to bowed geometries and back, appropriately applying suction and retraction of sliding member 100 moving material away from opening 50. Performance of various components and assemblies of catheter device 10A for such additional steps are described immediately herebelow.

Figure 5F:
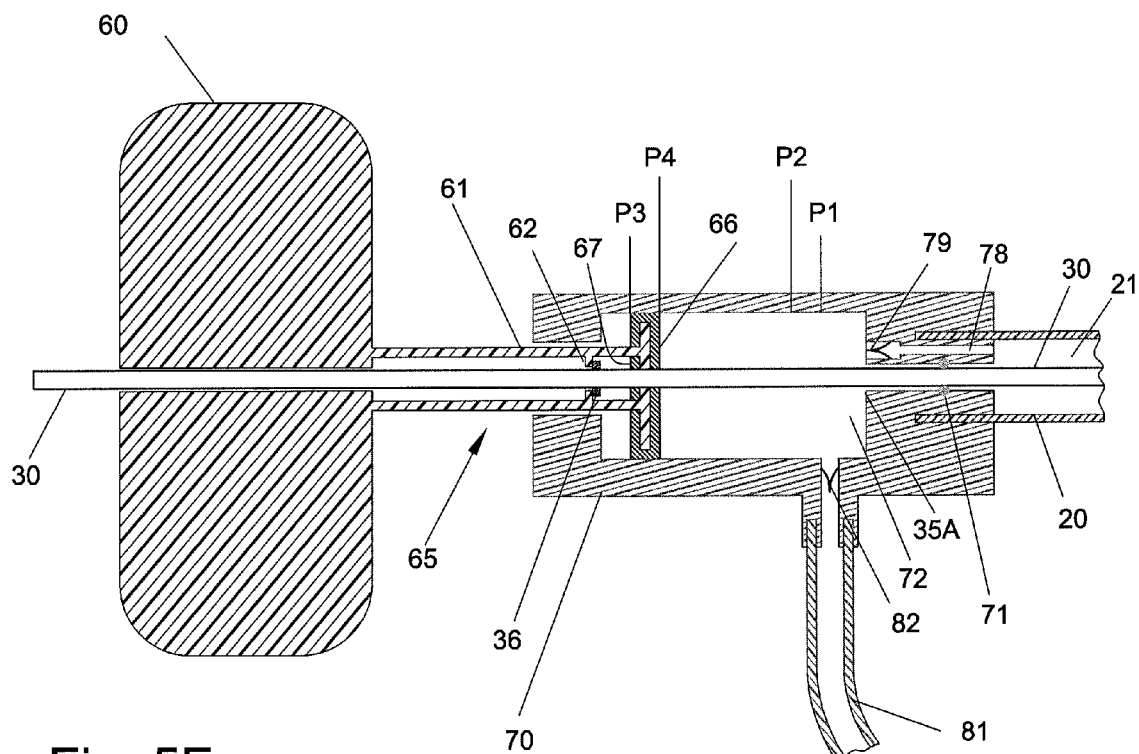
FIG. 5F is an enlarged sectional view of the proximal end of the catheter device of FIG. 5 shown with the grasper of the handle assembly shown in a partially advanced position.
Figure 5G:
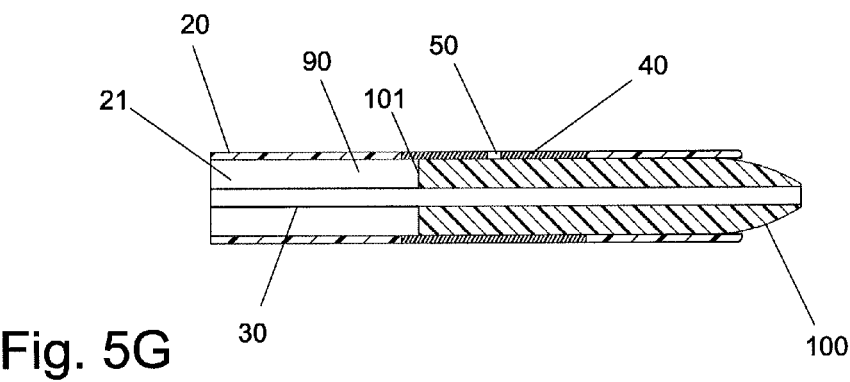
FIG. 5G is an enlarged sectional view of the distal end of the catheter device of FIG. 5 shown with the sliding member in the a partially advanced position corresponding to the grasper position of FIG. 5F.

Referring now to FIGS. 5F and 5G, grasper 60 has been advanced, causing plunger assembly 65 to advance from retracted position P3 to second intermediate position P4. Proximal edge 67 of plunger 66 has moved away from linkage projection 36 of linkage 30 and shaft projection 62 has reached and come in contact with linkage projection 36 such that further advancement of plunger assembly 65 will cause linkage 30 to advance. Linkage 30 did not yet advance as plunger assembly 65 advanced from retracted position P3 to intermediate position P4 therefore sliding member 100 remains in its fully retracted position wherein the proximal portion of sliding member 100 is contained within a lumen of controllably arcuate segment 40 such that controllably arcuate segment 40 is in a relatively straight geometry.

Advancement of plunger assembly 65 causes positive pressure to be generated in aspiration chamber 72 causing fluid and other material to be evacuated from aspiration chamber 72 thru waste valve 82 and waste exit 81 and into waste chamber 80. One way valve, aspiration valve 79 prevents the fluid and other material contained in aspiration chamber 72 from entering aspiration lumen 21.

Further advancement of plunger assembly 65 from second intermediate position P4 to advanced position P1, shown in FIGS. 5 and 5A, continue the generation of positive pressure to further evacuate the equivalent volume of fluid and material from aspiration chamber 72 into waste chamber 80. In addition to the positive pressure and material evacuation, linkage 30 is advanced. Because of the initial contact between shaft projection 62 and linkage projection 36 that occurs when plunger assembly 65 reaches second intermediate position P4, continued advancement to advanced position P1 causes linkage 30 to advance due to an urging force placed upon linkage projection 36 by shaft projection 62. Referring back to FIGS. 5 and 5A, when grasper 60 is fully advanced, its proximal end making contact with the distal end of handle 70, linkage 30 is fully advanced causing sliding member 100 to be fully advanced. As sliding member is advanced, the proximal portion moves out of controllably arcuate segment 40 allowing controllably arcuate segment 40 to transition from a relatively straight geometry to a relatively arcuate or bowed geometric shape.

Figure 6:
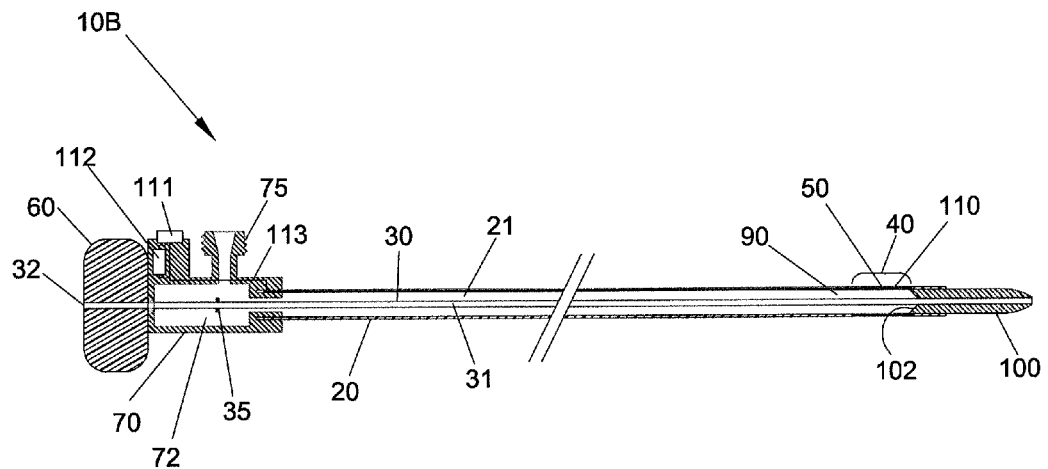
FIG. 6 is a cross-sectional view of another preferred embodiment of a catheter device constructed in accordance with the present invention.

FIG. 6 depicts another preferred embodiment of catheter device of the present invention which is similar to the catheter device 10 of FIGS. 1A and 1B with grasper 60, linkage 30 and sliding member 100 all in a fully advanced position. Accordingly, elements of this embodiment which are similar to elements of catheter device 10 of FIGS. 1A and 1B are referenced with the same reference numerals. Referring specifically to FIG. 6, catheter device 10B is shown with controllably arcuate segment 40 in its maximally straight geometry, and in this particular also preferred embodiment, controllably arcuate segment 40 is naturally biased to be in a maximally straight geometry as opposed to the normally curved bias of FIGS. 1A and 1b. Catheter device 10B includes an aspiration chamber 72 included in handle 70. Catheter shaft 20 is fixedly attached to handle 70 while creating a fluid path from aspiration port 75, into aspiration chamber 72 and continuing through aspiration lumen 21 to material collection chamber 90. Material collection chamber 90 is in fluid communication with opening 50 of controllably arcuate segment 40 and located proximal to opening 50. As shown in FIG. 6, material collection chamber 90 may be a simple continuation of aspiration lumen 21, or material collection chamber 90 may have a specific geometry or cavity-like structure while still in fluid communication with aspiration lumen 21. Material collection chamber may alternatively be fluidly isolated from aspiration lumen 21 such as by way of an integrated valve that allows aspiration lumen 21 to be in fluid communication with opening 50 when vacuum or suction is applied by way of aspiration port 75.

Present within an internal lumen of catheter shaft 20 is a flexible shaft, linkage 30, which is preferably a hollow tube permitting a guidewire to be inserted through its internal lumen, linkage lumen 31. Linkage 30 may be constructed of a flexible metal, such as a flexible steel hypotube, or a superelastic material such as Nitinol, a nickel titanium alloy in its superelastic state. Alternatively, linkage 30 may be constructed of a flexible plastic tube. As shown in FIG. 6, an opening around linkage 30 provides fluid communication between aspiration chamber 72 and aspiration lumen 21. At its proximal end, linkage 30 is fixed to grasper 60 which controls the advancement and retraction of linkage 30 and its connected components. Linkage 30 is fixed at its distal end to sliding member 100. The grasper 60, linkage 30 and sliding member 100 are shown in the fully advanced position and the controllably arcuate segment 40 is shown in a maximally bowed geometry. Sliding member 100 has a beveled, sharpened or otherwise tapered end, tapered cutting end 102 which faces opening 50 such that when sliding member 100 is retracted, material protruding through opening 50 can be severed from attached material located within opening 50 to prevent jamming of sliding member 100. In alternative embodiments, wherein opening 50 is distal to sliding member 100, tapered cutting end 102 would be located on the opposite end of sliding member 100, the distal end, such that when sliding member 100 is advanced, material protruding through opening 50 is similarly severed.

Grasper 60 surrounds and is fixedly attached to linkage 30. The proximal end of linkage 30 includes guidewire opening 32 into which a guidewire can be placed and from which a guidewire can exit if inserted from the other end. Linkage lumen 31 may include a valve, not shown, in its path to prevent leakage of blood or other fluid once catheter device 10B is inserted into the body. Alternatively, the diameter of linkage lumen 31 is chosen to be as small as possible, slightly larger than the outside diameter of the guidewire it is to be placed over. Linkage 30 enters handle 70 such that a relatively fluid tight seal is created, such as that created with an elastomeric o-ring which seals between handle 70 and linkage 30 yet allows linkage 30 to slide back and forth as grasper 60 is advanced and retracted as was described in reference to FIGS. 3 and 3a. Linkage 30 may include a mechanical stop, such as linkage stop 35, included on the outer diameter of linkage 30 to limit the maximum retraction distance of grasper 60. Linkage stop 35 is positioned along the outer diameter of linkage 30 such that when grasper 60 is retracted till linkage stop 35 is in contact with the inside surface of aspiration chamber 72, sliding member 100 is properly positioned within controllably arcuate segment 40, the advanced position shown in and described with FIGS. 6, 6A and 6B. In this preferred embodiment, the distal end of sliding member 100 extends beyond the distal end of catheter device 10 throughout the fully advanced and fully retracted travel of grasper 60 and linkage 30.

As mentioned previously, the catheter device 10B of FIG. 6 is constructed such that the normal bias of controllably arcuate segment 40 is a straight geometry, generally along the longitudinal axis of catheter shaft 20. It should be noted that in this and all other embodiments of this application, controllably arcuate segment 40 while naturally biased to be bowed or straight, is relatively flexible, i.e. flexible enough relative to its length to allow insertion of catheter device 10B through the body, such as through the vascular system, without disrupting or otherwise damaging the inner walls of conduits such as blood vessels. This flexibility may or may not be compromised when sliding member 100 is retracted to reside within a lumen of controllably arcuate segment 40. The catheter device 10B of FIG. 6 further includes means to change controllably arcuate segment 40 from its naturally straight geometry to a relatively bowed or curved geometry. Various curving means are described in accordance with the FIGS. 6, 6A, 6B and 7 through 10 however it should be understood and considered within the scope of this application, that numerous alternatives are possible to cause, based on controls that can be activated from the proximal end of catheter device 10, such as those on or near handle 70, shape transformation of controllably arcuate segment 40.

Figure 6A:
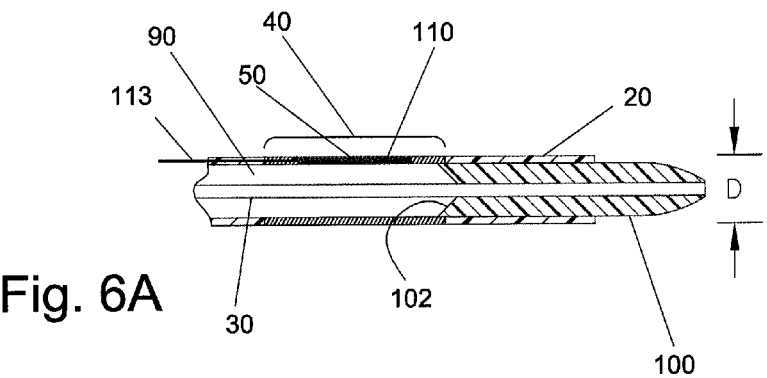
FIG. 6A is an enlarged sectional view of the distal end of the catheter device of FIG. 6 shown with the controllably arcuate segment in a relatively straight geometric shape.
Figure 6B:
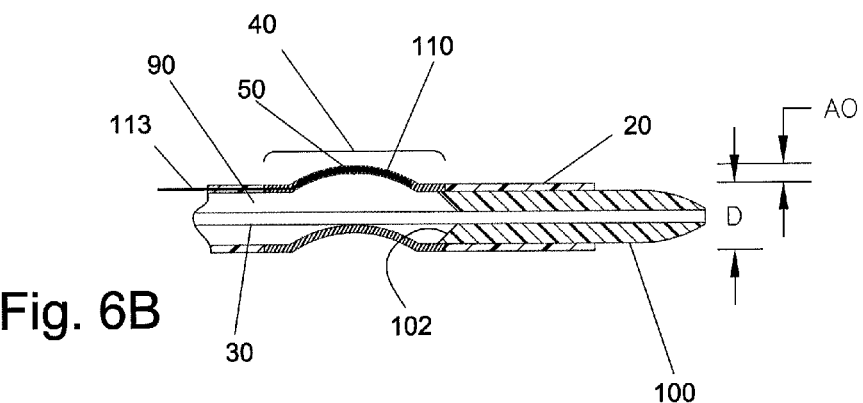
FIG. 6B is an enlarged sectional view of the distal end of the catheter device of FIG. 6 shown with the controllably arcuate segment in a relatively bowed geometric shape.

Again, referring specifically to FIG. 6 and additionally to FIGS. 6A and 6B, contained or embedded within the walls of controllably arcuate segment 40 is curving element 110 which can on command convert controllably arcuate segment 40 from a relatively straight geometry to a relatively bowed geometry. The curving element 110 is preferably an electrically activatable component such as a piezo element, an electromagnetic assembly or a shaped memory component, such as a shaped memory alloy or shaped memory polymer. When connected to an energy source applying a voltage and or a driving current, curving element 110 changes its shape thus causing controllably arcuate segment 40 to also change shape. Curving element 110 is attached to controls in handle 70 by arcuate control wires 113, preferably flexible electrical conductors, such as wires, embedded in or on the inside diameter of shaft 20. At the proximal end of arcuate control wires 113 is an energy source, power source 112, which is preferably an integrated battery or battery assembly. Completing the electrical circuit is a switch, arcuate control switch 111, which when depressed by the user, fully connects power source 112 to curving element 110 thus causing both curving element 110 and controllably arcuate segment 40 to change geometry such as changing from a relatively straight geometry to a relatively curved geometry. It should be noted, however, that a similar configuration of curving element 110 can be used to change controllably arcuate segment 40 from a relatively bowed geometry to a relatively straight geometry when power is applied to curving element 110. FIG. 6A depicts curving element 110 without power attached, i.e. arcuate control switch 111 not depressed, and controllably arcuate segment 40 in a relatively straight geometry. FIG. 6B depicts curving element 110 with power attached, i.e. arcuate control switch 111 depressed by the operator, and controllably arcuate segment 40 in a relatively bowed geometry. It may be desirable to add an indicator, not shown, to indicate the geometric shape of controllably arcuate segment 40 when the catheter device of the present invention is inserted into the patient, i.e. when the controllably arcuate segment 40 cannot be directly visualized. The shape indicating means, all not shown, may include a visual indicator, such as an indicator light located on the handle of the device, and or an audio indicator such as an electronic buzzer which generate feedback to the user to indicate the geometric shape of controllably arcuate segment 40. For example, since the catheter device of the present invention is generally not to be advanced or retracted unless controllably arcuate segment 40 is in a relatively straight geometric shape, an audio indicator may be included which creates a buzzing sound whenever the controllably arcuate segment 40 is not in a relatively straight geometric shape.

Still referring to FIG. 6, sliding member 100 is shown in its fully advanced position, since grasper 60 is fully advanced causing linkage 30 to also be fully advanced. Controllably arcuate segment 40 has a normally straight geometric bias, and is converted to a relatively bowed geometry by activation of curving element 110 as well as being converted back to a relatively straight geometry by deactivation of curving element 110. Unlike the catheter device 10 of FIG. 1, sliding member 100 does not have to be used to change the shape of a pre-curved controllably arcuate segment 40. Sliding member 100 in FIG. 6 still however provides the function of moving material away from opening 50 when retracted, aided by a sharpened leading edge, tapered cutting end 102. Since sliding member 100 of catheter device 10B of FIG. 6 does not provide the function of changing the shape of controllably arcuate segment 40, sliding member 100 can be made of very flexible materials which do not impact the shape of controllably arcuate segment 40 when sliding member 100 enters and exits the lumen of controllably arcuate segment 40. When controllably arcuate segment 40 is in its maximally bowed geometry as caused by curving element 110, and vacuum is applied at opening 50 thus drawing material through opening 50, sliding member 100 can be retracted pushing material away from opening 50 without altering the shape of controllably arcuate segment 40.

Referring specifically to FIGS. 6A and 6B, catheter shaft 20 has a diameter, catheter diameter D, near its distal end. When controllably arcuate segment 40 has a relatively curved geometry, the maximum offset from the outside diameter of catheter shaft 20 is defined as axial offset AO. In cardiovascular applications, catheter diameter D will typically between 1.5 and 4 millimeters. Curving element 40 has a length and radius of curvature of both its proximal and distal arc that are chosen to create a group of products that provide a wide range of values for axial offset AO. Typically catheter diameter D is chosen to be applicable to navigate the tortuosity of the vasculature to reach the target lesion to be treated, and axial offset AO is chosen to cause the opening 50 to be in contact, with sufficient force, to the target lesion when controllably arcuate segment 40 is in its maximally bowed geometry. Some applications, such as interventional neurological procedures, may require much smaller diameters and axial offsets, while other applications may permit or require larger diameters and offsets.

Figure 7:
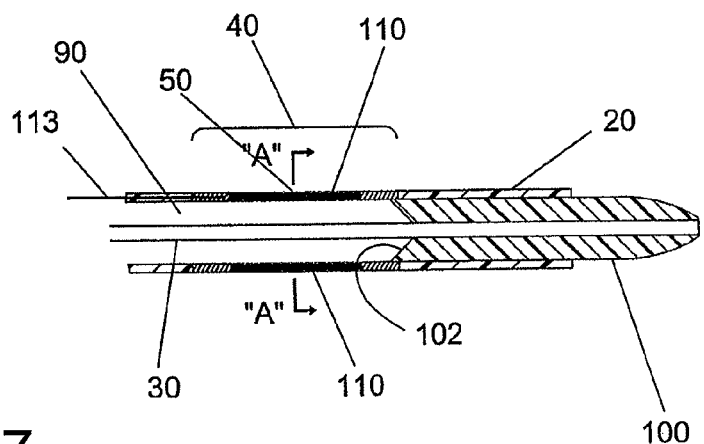
FIG. 7 is an enlarged sectional view of the distal end of another preferred embodiment of the catheter device of the present invention.

FIG. 7 depicts another preferred embodiment of catheter device of the present invention which is similar to the catheter device of FIG. 6 with an integral means for curving controllably arcuate segment 40, curving means 110 embedded within the walls of controllably arcuate segment 40. As described previously, curving means 110 can be of various shape altering forms, such as shaped memory components, piezo components, electromagnetic assemblies and other electrically and non electrically activated shape changing components known to those of skill in the art, and all considered within the scope of this application. Curving means 110 is attached to electrical controlling wires, arcuate control wires 113 which connect to power and switching means contained in the proximal handle. Controllably arcuate segment 40 also includes one or more holes, opening 50 which are in fluid communication with a chamber, material collection chamber 90, into which material received through opening 50 is pushed by tapered cutting end 102 of sliding member 100. Linkage 30 and sliding member 100 are shown in their fully advanced position. FIG. 7 defines a cross-sectional view A-A directed toward the distal end of catheter shaft 20.

Figure 8:
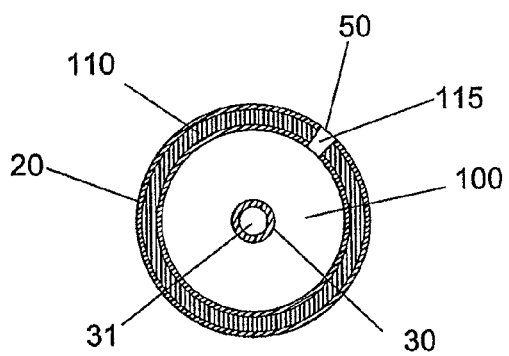
FIG. 8 is an enlarged sectional view taken along line A-A of FIG. 7 showing a preferred configuration of a curving element.

FIG. 8 shows a preferred embodiment of the curving element 110 located near the distal end of catheter shaft 20 shown at the cross-sectional view A-A of FIG. 7. The curving element 110 of FIG. 8 has a tubular construction, with a circular cross section contained within the walls of catheter shaft 20 in the region of controllably arcuate segment 40. Alternatively but not shown, curving element 110 may be outside of the walls within the lumen of catheter shaft 20. Curving element 110 would include a thru-hole or opening, curving element opening 115 which is aligned with opening 50 to allow material to pass through opening 50 and curving element opening 115 from the outside of catheter shaft 50 to an inner lumen of catheter shaft 20 when suction is applied. Curving element 110 is controlled from the proximal end of catheter device 10, such as has been described hereabove, and its tubular structure changes shape to cause controllably arcuate segment 40 to change from a relatively straight geometry to a relatively bowed geometry or causes controllably arcuate segment 40 to change from a relatively bowed geometry to a relatively straight geometry. Curving element 110 may be attached to electrical wires connected to a switch and power supply as described in FIGS. 6, 6A and 6B or other activation means controllable from the proximal end of catheter device 10.

Figure 9:
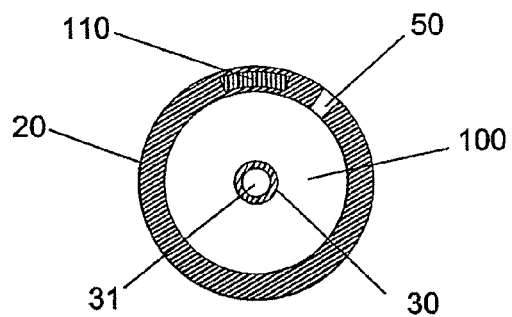
FIG. 9 is an enlarged sectional view taken along line A-A of FIG. 7 showing another preferred configuration of a curving element.

FIG. 9 shows another preferred embodiment of the curving element 110 located near the distal end of catheter shaft 20 shown at the cross-sectional view A-A of FIG. 7. The curving element 110 of FIG. 8 has a filament-like construction, with a chord-like cross section contained within the walls of catheter shaft 20 in the region of controllably arcuate segment 40. Alternatively but not shown, curving element 110 may be outside of the walls within the lumen of catheter shaft 20. Curving element 110 would be placed away from opening 50 such that material will pass through opening 50 from the outside of catheter shaft 20 to an inner lumen of catheter shaft 20 when suction is applied. Curving element 110 is controlled from the proximal end of catheter device 10, such as has been described hereabove, and its filament-like structure changes shape to cause controllably arcuate segment 40 to change from a relatively straight geometry to a relatively bowed geometry or cause controllably arcuate segment 40 to change from a relatively bowed geometry to a relatively straight geometry. Curving element 110 may be attached to electrical wires connected to a switch and power supply as described in FIGS. 6, 6A and 6B or other activation means controllable from the proximal end of catheter device 10.

Figure 10:
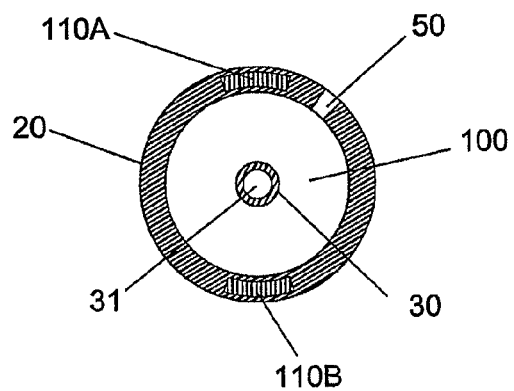
FIG. 10 is an enlarged sectional view taken along line A-A of FIG. 7 showing yet another preferred configuration of a curving element.

FIG. 10 shows yet another preferred embodiment of the curving element 110 located near the distal end of catheter shaft 20 shown at the cross-sectional view A-A of FIG. 7. The curving element of FIG. 10 consists of two curving elements, first curving element 110A and second curving element 110B both of which have a filament-like construction, with a chord-like cross section contained within the walls of catheter shaft 20 in the region of controllably arcuate segment 40. First curving element 110A and second curving element 110B may have different lengths and or cross-sectional geometries, and they may be controlled together or independently. Alternatively but not shown, first curving element 110A and or second curving element 110B may be outside of the walls within the lumen of catheter shaft 20. Both first curving element 110A and second curving element 110B would be placed away from opening 50 such that material will pass through opening 50 from the outside of catheter shaft 50 to an inner lumen of catheter shaft 20 when suction is applied. Both first curving element 110A and second curving element 110B is controlled from the proximal end of catheter device 10, such as has been described hereabove, and the filament-like structures change shape to cause controllably arcuate segment 40 to change from a relatively straight geometry to a relatively bowed geometry or cause controllably arcuate segment 40 to change from a relatively bowed geometry to a relatively straight geometry. Independent control of first curving element 110A and second curving element 110B can be used to create multiple states of curvature for controllably arcuate segment 40 such as to cause different axial offsets as has been described hereabove. Both first curving element 110A and second curving element 110B may be attached to electrical wires connected to a switch and power supply as described in FIGS. 6, 6A and 6B or other activation means controllable from the proximal end of catheter device 10.

Referring collectively to all of the figures and their descriptions included hereabove, the catheter devices of the present invention are intended to enter the body of a mammalian patient, such as via percutaneous or surgical means, to perform a therapeutic or diagnostic procedure. To properly accomplish these types of procedures, the devices would be provided in a sterile condition, with appropriate packaging to maintain sterility up until use. In addition, the catheter device may be part of a kit, with numerous other components applicable to the procedure, such as a guide catheter and guidewire, included in the sterile packaging or in separate sterile packaging included in the same purchased kit. The catheter device of the present invention may be inserted into the body over a standard interventional guidewire to assist in advancing the device to the intended location. The various figures and included text have described configurations wherein the device has a guidewire that enters and exits the catheter at or near the distal and proximal ends. Devices with this configuration utilize guidewires which are approximately twice the length of the over the wire device to allow placement of the device with a pre-placed guidewire and withdrawal of the device leaving the guidewire in place. In an alternative catheter design, also considered within the scope of this application, near the distal end of the catheter device is included a small length of material attached to the catheter shaft, similar to a sidecar, which consists of a single lumen and its surrounding walls. In this configuration, a smaller length guidewire can be inserted through the lumen of the sidecar only, not through the entire length of the catheter device, and the catheter device advanced and retracted over this shorter guidewire.

The catheter of this invention may be a precursor to other material removal or treatment procedures such as balloon angioplasty, stenting or other procedures. Although this system was described specifically for a saphenous vein graft, it is readily applicable to any stenosis of a vessel or other applicable tubular body conduit in the body. For example, the catheter device of the present invention could be used to open stenoses in the carotid artery, dialysis fistulas, peripheral vasculature, etc. Although the present invention has only described the removal of plaque or thrombus from human vessels, the catheter device of the present invention could also be used to remove other stenotic or occluding tissue from ducts such as the ureters or the fallopian tubes. Mammalian patients would include both humans and other animals. Also, although percutaneous procedures have been described, catheter devices of the present invention, particularly those with larger diameters or where the intended site is a body conduit that is not a blood vessel, could be used intraoperatively by surgical incision into an access point appropriate for the intended site.

In order to draw material through opening 50, a negative pressure is applied to the inner side of opening 50 which is communicated through a lumen within catheter shaft 20. Various means of causing this negative pressure, also referred to synonymously throughout this application as vacuum, suction or aspiration, can be used. Vacuum generators can be integral to catheter device such as has been described in reference to FIGS. 5 and 5A through 5G, or external vacuum generators can be attached including a simple syringe to more complex aspiration and material collection devices. The various embodiments described hereabove show a fluid communication between aspiration lumen 21 and opening 50 that is connected via material collection chamber 90. It should be understood and considered within the scope of this application that aspiration lumen 21 can be connected directly to opening 50 and material collection chamber 90 isolated from the negative pressure by way of a valve or other means. This particular configuration is another preferred embodiment and may be useful in avoiding clogging or otherwise obstructing aspiration lumen 21 from being able to apply the appropriate amount of suction at opening 50. Opening 50 may include one or more holes with various cross-sectional geometries and tapers. Opening 50 may be designed to be fluidly closed when controllably arcuate segment 40 is in a relatively straight geometry and open as controllably arcuate segment 40 transforms to a bowed geometry, or opening 50 may be fluidly open at all times.

Also, it is intended for opening 50 to be brought in close proximity to the material to be removed, and apply a finite amount of force to the wall of the body conduit or on the material to be removed by the portion of catheter shaft 20 immediately surrounding the opening, each feature intended to enhance the ability of the vacuum to draw material through opening 50. This proximity is achieved when controllably arcuate segment 40 is changed from a relatively straight geometry to a relatively bowed geometry. The various embodiments described hereabove show various configurations of relatively bowed geometries, however it should be understood and considered within the scope of this application that any geometry that causes an axial offset of opening 50 from the outer surface of the majority of catheter shaft 20 would function to bring opening 50 towards the wall of the biological conduit into which it is inserted. It also should be understood that controllably arcuate segment 40 may be able to assume multiple geometries with multiple axial offsets or other geometric configurations that provide specific advantages for the various anatomies and disease states and locations being treated. It is preferred that a portion of catheter shaft 20 extend beyond controllably arcuate segment 40 such that a portion of non shape altering catheter shaft exists between the distal tip of catheter shaft 20 and controllably arcuate segment 40.

In the various procedures described hereabove, it may be desirable to remove material such as thrombus that may be present at the end of catheter shaft 20. To facilitate this function, a lumen may be provided to support simple suction removal from the end of the catheter shaft 20, or an internal mechanism or a removable core, such as linkage 30 and sliding member 100 may be removable to create a lumen to which suction can be applied to remove material from the distal end of the catheter.

In another preferred embodiment of the present invention, a catheter device includes an elongate catheter body or shaft having a proximal end and a distal end, a controllably arcuate segment, an aspiration chamber located near the proximal end of the catheter shaft, a controllably arcuate segment including at least one opening and an aspiration lumen in fluid communication with the aspiration chamber and one or more of the openings in the controllably arcuate segment. This particular catheter device may include a separate lumen to allow over the wire insertion and a lumen to allow aspiration from the distal tip of the catheter.

The various embodiments described hereabove, such as those described in reference to FIGS. 5 and 5A through 5G, have described a catheter device 10A wherein retraction of grasper 60 causes linkage 30 and thus sliding member 100 to also retract to accomplish one or more functions including moving material away from opening 50 in a proximal direction and into material collection chamber 90 which is proximal to opening 50. It should be appreciated and considered within the scope of this application wherein material collection chamber 90 is distal to opening 50, and advancement of grasper 60 causes advancement of linkage 30 and thus sliding member 100 such that material is moved away from opening 50 in a distal direction into material collection chamber 90. In this particular configuration, sliding member 100 would not exit the distal end of catheter shaft 20 but would remain within a lumen of catheter shaft 20 in both its fully advanced and fully retracted positions. Similar to other embodiments, material is drawn through opening 50 via suction from the proximal end of catheter device 10, such as via aspiration port 75 and aspiration lumen 71.

It is to be understood and appreciated that the invention has been described herein with reference to certain presently preferred embodiments and examples only, and no effort has been made to exhaustively describe all possible embodiments and examples of the invention. Indeed, as those killed in the art will appreciate, various additions, deletions, modifications and variations may be made to the particular embodiments and examples described hereabove without departing from the intended spirit and scope of the invention. In addition, wherever steps of a method have been described, there is no intent for a required order unless specifically described. Accordingly, it is intended that all such additions, deletions, modifications and variations be included within the scope of the following claims.

What is claimed is:

1. A transluminal method for removing material from a biological conduit, said method comprising the steps of:
   providing a catheter device that comprises:
      an elongated catheter shaft having a proximal end and a distal end; and
      a controllably arcuate segment defining at least one opening in fluid communication with the proximal end;
   percutaneously or surgically inserting and transluminally advancing the catheter into the biological conduit;
   subsequently changing the controllably arcuate segment from a relatively straight shape to a bowed shape, the bowed shape being formed by arcing the arcuate segment in a first direction to create external convex and concave surfaces of the arcuate segment in the first direction where the proximal and distal ends of the catheter shaft remain aligned along a longitudinal axis of the catheter; and
   subsequently applying suction to the at least one opening in the controllably arcuate segment.

2. The method of claim 1, wherein the catheter includes a sliding member movable within the elongated catheter shaft and arcuate segment, and the method further comprises:
   retracting the sliding member to move an occlusive material received through the opening into the material collection chamber away from the at least one opening and toward the proximal end of the elongated catheter shaft.

3. The method of claim 2, wherein movement of the sliding member past the arcuate segment allows the transition from the relatively straight shape to the bowed shape.

4. The method of claim 1, wherein the controllably arcuate segment defines at least one opening in the form of a hole that is located at the convex portion of the controllably arcuate segment when the arcuate segment takes the bowed shape.

5. The method of claim 1, wherein the at least one opening is completely located in a portion of the arcuate segment that maintains a substantially constant cross section throughout the transition from the bowed shape to the relatively straight shape.

6. The method of claim 1, wherein the at least one opening is located near the distal end of the elongated catheter shaft.

7. The catheter of claim 1, wherein the controllably arcuate segment has a normally bowed bias, and the method includes positioning the sliding member within the controllably arcuate segment to cause the arcuate segment to take the relatively straight shape.

8. The method of claim 1, further comprising, when the controllably arcuate segment takes the bowed shape, maintaining substantially straight portions of the elongated catheter shaft on both sides of the arcuate segment that are co-axial with a longitudinal axis.

* * * * *